(12) United States Patent
Li et al.

(10) Patent No.: US 7,781,757 B2
(45) Date of Patent: Aug. 24, 2010

(54) ORGANIC SEMICONDUCTOR MATERIAL, ORGANIC SEMICONDUCTOR ELEMENT AND FIELD EFFECT TRANSISTOR USING THE SAME

(75) Inventors: Jian Li, Moriguchi (JP); Yasuko Hirayama, Moriguchi (JP); Takeshi Sano, Moriguchi (JP); Hiroyuki Fujii, Moriguchi (JP); Kenichirou Wakisaka, Moriguchi (JP)

(73) Assignee: Sanyo Electric Co., Ltd., Osaka (JP)

( * ) Notice: Subject to any disclaimer, the term of this patent is extended or adjusted under 35 U.S.C. 154(b) by 1011 days.

(21) Appl. No.: 11/507,607

(22) Filed: Aug. 22, 2006

(65) Prior Publication Data
US 2007/0045618 A1    Mar. 1, 2007

(30) Foreign Application Priority Data

| Aug. 24, 2005 | (JP) | ............................. 2005-243220 |
| Aug. 29, 2005 | (JP) | ............................. 2005-248003 |
| Jul. 28, 2006 | (JP) | ............................. 2006-205832 |
| Aug. 9, 2006 | (JP) | ............................. 2006-217277 |
| Aug. 9, 2006 | (JP) | ............................. 2006-217278 |

(51) Int. Cl.
   *H01L 35/24* (2006.01)
   *H01L 51/00* (2006.01)
   *H01L 23/58* (2006.01)
   *H01L 21/00* (2006.01)
   *C07D 333/12* (2006.01)
   *C07D 333/20* (2006.01)

(52) U.S. Cl. .................. 257/40; 257/E51.051; 257/642; 549/74; 438/82; 438/99

(58) Field of Classification Search .................. 528/380; 257/40, E51.051; 549/74
See application file for complete search history.

(56) References Cited

U.S. PATENT DOCUMENTS 7,153,980 B2 * 12/2006 Ohba et al. .................. 549/68

7,166,859 B2    1/2007 Hirose et al.

(Continued)

FOREIGN PATENT DOCUMENTS

CN    1619855    5/2005

(Continued)

OTHER PUBLICATIONS

Kunugi et al, Light-emitting diodes based on linear and starburst electro-oligomerized thienyltriphenylamines, Synthetic Metals, 89, 1997, 227-229.*

Bender et al, Effect of Substitution on the Electrochemical and Xerographic properties of Triarylamines: Correlation to the Hammett Parameter of the Substituent and Calculated HOMO Energy Level; Chem Mater, 2001, 13, 4105-4111.*

(Continued)

*Primary Examiner*—Randy Gulakowski
*Assistant Examiner*—Rachel Kahn
(74) *Attorney, Agent, or Firm*—NDQ & M Watchstone LLP

(57) ABSTRACT

An organic semiconductor material comprising an amine unit having a secondary or tertiary amine structure and a thiophene unit having a thiophene ring structure and preferably the amine unit has the following structure:

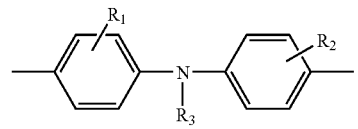

wherein $R_1$, $R_2$, and $R_3$ independently represent hydrogen, an optionally substituted alkyl group, an optionally substituted alkoxy group, an optionally substituted ether group, or an optionally substituted aryl group and may be same or different from each other.

4 Claims, 6 Drawing Sheets

U.S. PATENT DOCUMENTS 7,307,277 B2 * 12/2007 Frey et al. .................. 257/40
7,348,428 B2 *  3/2008 O'Dell et al. ............. 544/209

FOREIGN PATENT DOCUMENTS

| | | |
|---|---|---|
| JP | 2004-006782 | 1/2004 |
| JP | 2005-513788 | 5/2005 |
| WO | WO 03/052841 A1 | 6/2003 |

OTHER PUBLICATIONS

Chinese Office Action, dated Sep. 4, 2009; English translation included.

* cited by examiner

ORGANIC SEMICONDUCTOR MATERIAL, ORGANIC SEMICONDUCTOR ELEMENT AND FIELD EFFECT TRANSISTOR USING THE SAME

BACKGROUND OF THE INVENTION

1. Field of the Invention

The invention relates to an organic semiconductor material and an organic semiconductor element using the material.

2. Description of the Related Art

Along with studies of an organic semiconductor, studies in which an organic semiconductor material is used for a semiconductor element conventionally using a Si material such as a transistor have been examined in recent years to use. The organic semiconductor material is usable for vapor deposition at a relatively low temperature, and while being in form of a solution, the material is also suitable for formation of a semiconductor layer by a printing method such as an ink-jet manner. Accordingly, as compared with the case of using Si material, a semiconductor element can be produced by a simple process.

Japanese Patent Application Laid-Open (JP-A) No. 2005-513788 proposes a polyarylamine or a polymer having a thiophene structure as the semiconductor material.

JP-A No. 2004-6782 proposes a branched type conjugation polymer having a conjugated bond between a main chain and a side chain as the semiconductor material.

However, a conventional organic semiconductor material is insufficient in the carrier mobility and so far, an organic semiconductor material having higher carrier mobility is desired.

SUMMARY OF THE INVENTION

An object of the invention is to provide an organic semiconductor material with high carrier mobility and an organic semiconductor element using the material.

<First Aspect of the Invention>

An organic semiconductor material according to the first aspect of the invention consists of an amine unit having a secondary or tertiary amine structure and a thiophene unit having a thiophene ring structure.

According to the invention, a semiconductor material with high carrier mobility can be provided, and when the material is used for an organic transistor element, excellent transistor properties can be obtained.

The organic semiconductor material of the invention is characterized by preferably having an amine unit with the following structure:

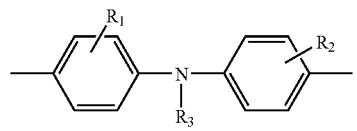

wherein $R_1$, $R_2$, and $R_3$ independently represent hydrogen, an optionally substituted alkyl group, an optionally substituted alkoxy group, an optionally substituted ether group, or an optionally substituted aryl group and may be same or different from each other.

In the optionally substituted alkyl group, optionally substituted alkoxy group, and optionally substituted aryl group, the substituent group may be substituent groups containing an element such as oxygen, nitrogen, silicon, phosphorus, and sulfur. The aryl group may include a phenyl group and a naphthyl group.

The organic semiconductor material of the invention is characterized by preferably having the following structure:

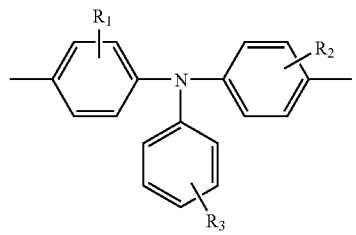

wherein $R_1$, $R_2$, and $R_3$ independently represent hydrogen, an optionally substituted alkyl group, an optionally substituted alkoxy group, an optionally substituted ether group, or an optionally substituted aryl group and may be same or different from each other.

Further, the organic semiconductor material of the invention may have an amine unit with the following structure:

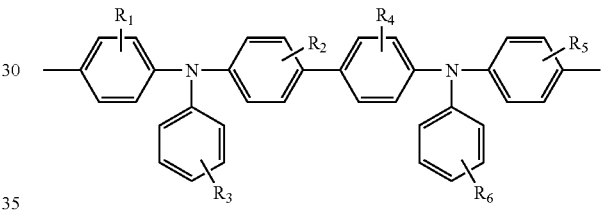

wherein $R_1$ to $R_6$ independently represent hydrogen, an optionally substituted alkyl group, an optionally substituted alkoxy group, an optionally substituted ether group, or an optionally substituted aryl group and may be same or different from each other.

Further, the organic semiconductor material of the invention is characterized by preferably having the thiophene unit with the following structure:

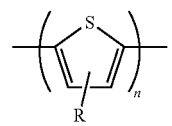

wherein R represents hydrogen, an optionally substituted alkyl group, an optionally substituted alkoxy group, an optionally substituted ether group, or an optionally substituted aryl group and n is an integer of 1 to 20.

The organic semiconductor material of the invention may have an asymmetric or symmetric chemical structure.

Further, a terminal of the chemical structure may be substituted with a substituent group mainly comprising a hydrocarbon such as an alkyl group, an alkoxy group, and an ether group. When a thiophene unit exists at a terminal of the chemical structure, the thiophene unit may be substituted with an alkyl group, an alkoxy group, and an ether group. The number of carbon atom of the alkyl is preferably 2 or more. If the number of carbon atom of the alkyl is preferably 2 or more, the organic semiconductor material can be easily dissolved in an organic solvent.

Examples of the organic semiconductor material according to the invention include those having the following structure:

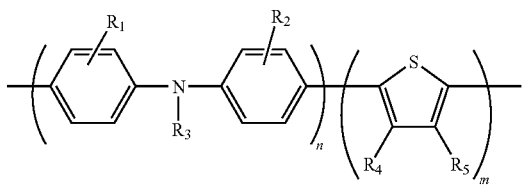

wherein $R_1$ to $R_5$ independently represent hydrogen, an optionally substituted alkyl group, an optionally substituted alkoxy group, an optionally substituted ether group, or an optionally substituted aryl group and may be same or different from each other; and m and n are an integer of 1 to 20.

Further, examples of the organic semiconductor material according to the invention include those having the following structure:

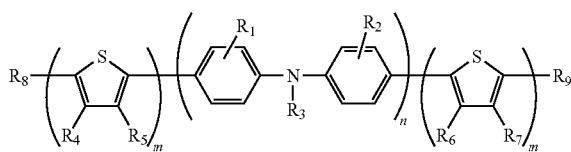

wherein $R_1$ to $R_9$ independently represent hydrogen, an optionally substituted alkyl group, an optionally substituted alkoxy group, an optionally substituted ether group, or an optionally substituted aryl group and may be same or different from each other; and m and n are an integer of 1 to 20.

Further, examples of the organic semiconductor material according to the invention include those having the following structure:

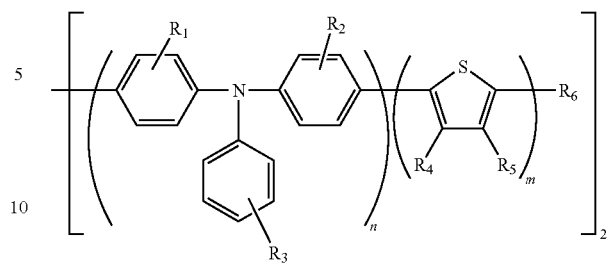

wherein $R_1$ to $R_6$ independently represent hydrogen, an optionally substituted alkyl group, an optionally substituted alkoxy group, an optionally substituted ether group, or an optionally substituted aryl group and may be same or different from each other; and m and n are an integer of 1 to 20.

Further, examples of the organic semiconductor material according to the invention include those having the following structure:

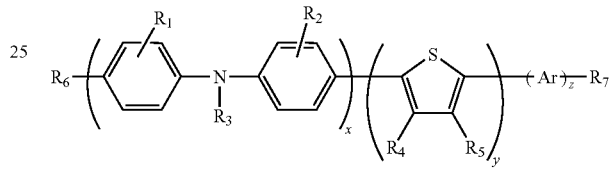

wherein Ar represents an optionally substituted aryl group; $R^1$ to $R^7$ independently represent hydrogen, an optionally substituted alkyl group, an optionally substituted alkoxy group, an optionally substituted ether group, or an optionally substituted aryl group and may be same or different from each other; and x, y, and z independently indicate a mole ratio of each unit.

Examples of the aryl represented by Ar may include aromatic or condensed cyclic compounds such as benzene, naphthalene, anthracene, tetracene, pentacene, fluorene, and carbazole.

Specific examples of the organic semiconductor material of the invention include the following:

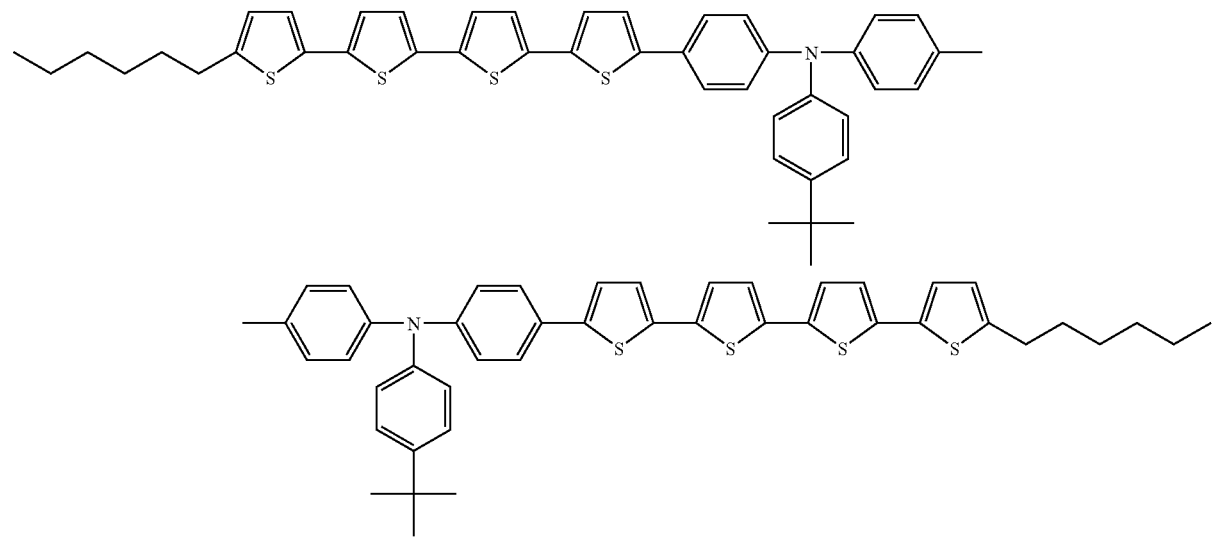

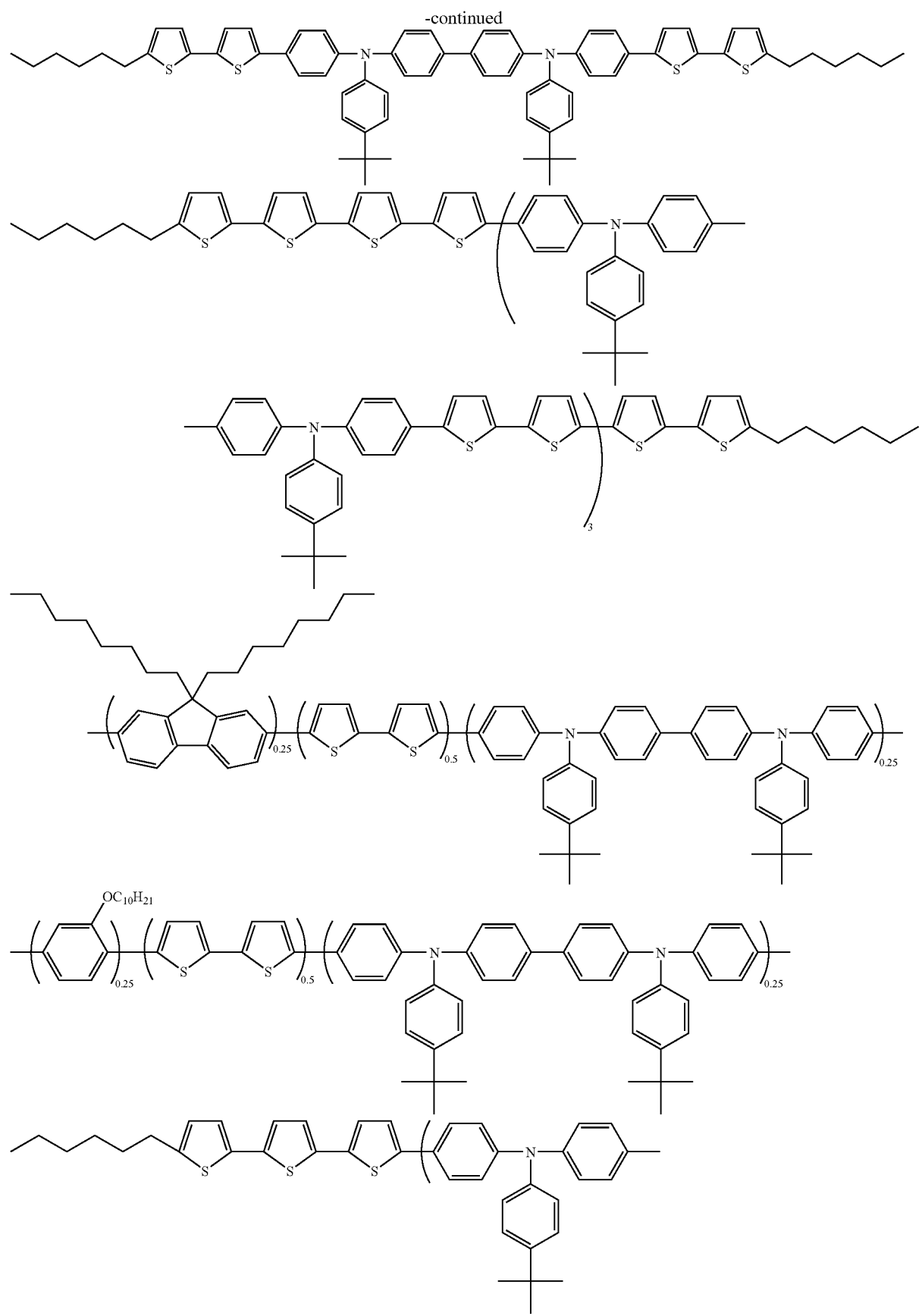

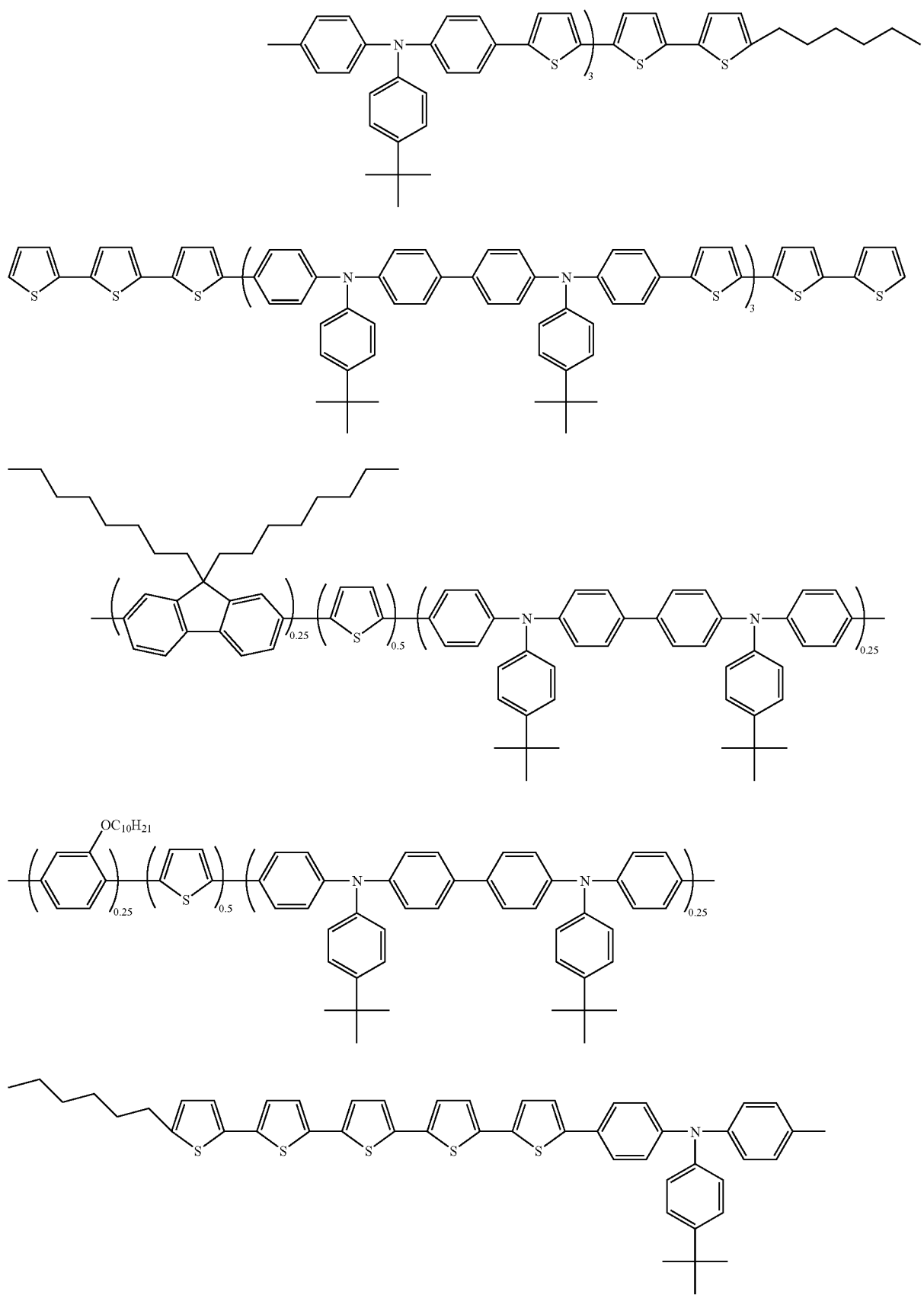

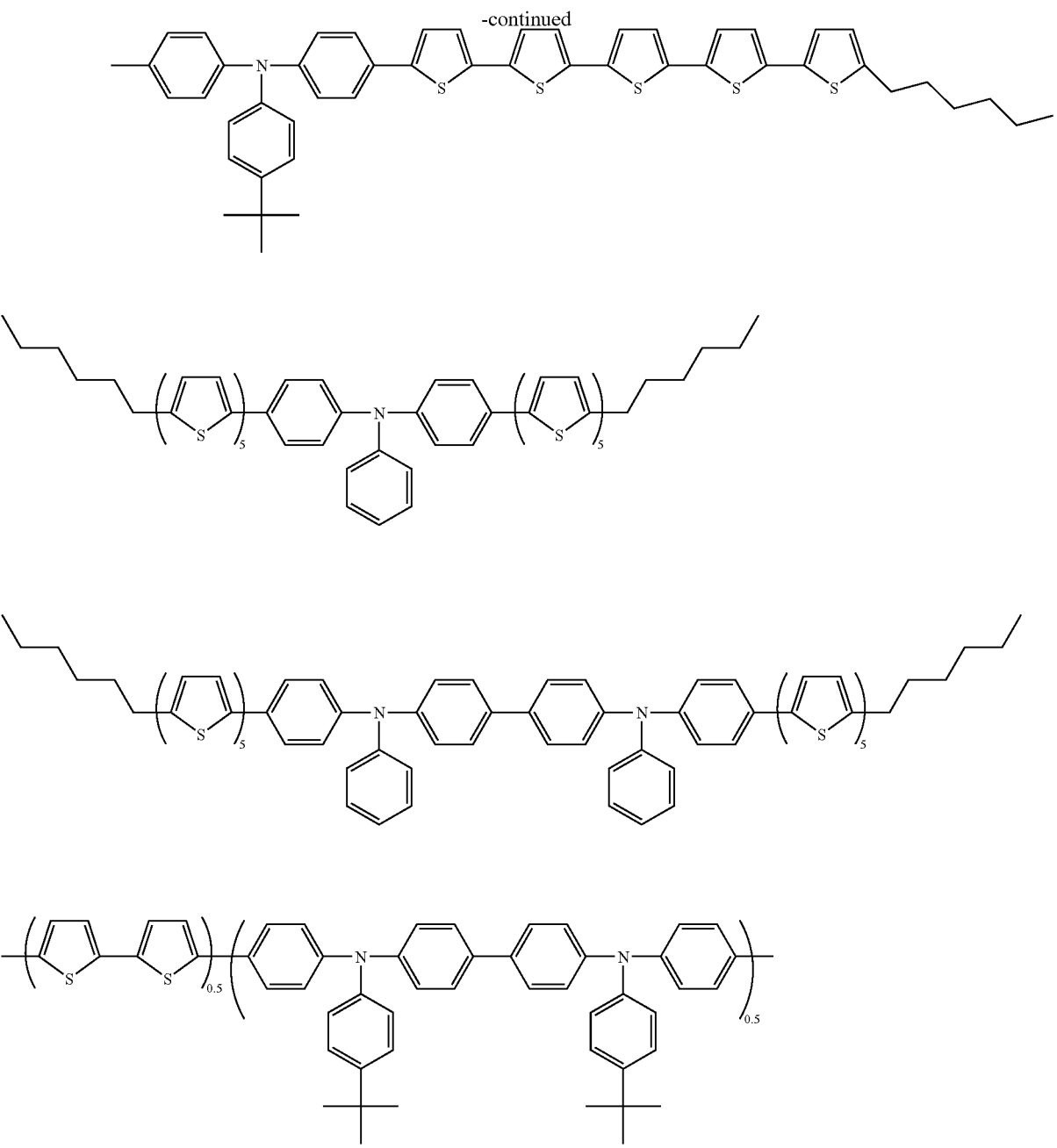
The amine unit in the organic semiconductor material of the invention may be those having the following structures:
wherein $R_1$ to $R_4$ independently represent hydrogen, an optionally substituted alkyl group, an optionally substituted alkoxy group, or an optionally substituted aryl group and may be same or different from each other:
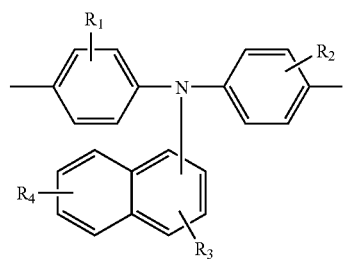
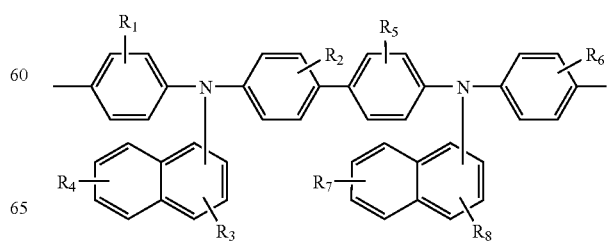

wherein $R_1$ to $R_8$ independently represent hydrogen, an optionally substituted alkyl group, an optionally substituted alkoxy group, an optionally substituted ether group, or an optionally substituted aryl group and may be same or different from each other.

The thiophene unit in the organic semiconductor material of the invention may be those having the following structures. In the following structures, $R^1$ to $R^3$ independently represent hydrogen, an optionally substituted alkyl group, an optionally substituted alkoxy group, an optionally substituted ether group, or an optionally substituted aryl group and may be same or different from each other; and n is an integer of 1 to 20.

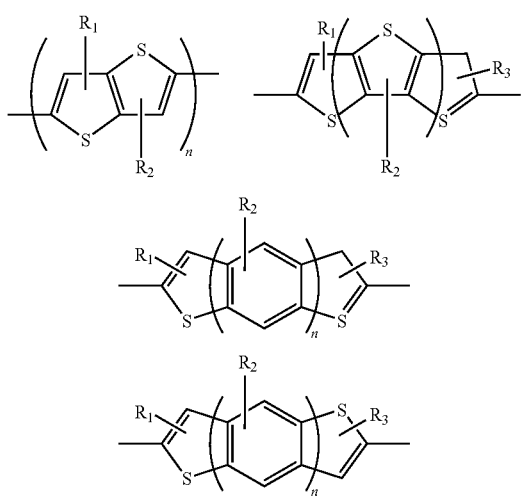

An organic semiconductor element of the invention is characterized by using the organic semiconductor material of the invention.

An organic transistor of the invention is characterized by using the organic semiconductor material of the invention.

A field effect transistor of the invention is a field effect transistor comprising a charge transporting material layer and a gate electrode directly or indirectly contacting the charge transporting material layer and controlling electric current in the charge transporting material layer by applying an electric field between the gate electrode and the charge transporting material layer, wherein the charge transporting material layer is formed using the above-mentioned organic semiconductor material of the invention.

<Second Aspect of the Invention>

An organic semiconductor material according to the second aspect of the invention is characterized by binding groups X1, X2, and X3 having an aromatic ring to a branching part Y having at least three binding parts.

According to the invention, a semiconductor material with high carrier mobility can be provided, and when the material is used for an organic transistor element, excellent transistor properties can be obtained.

The organic semiconductor material of the invention is characterized by preferably having the branching part Y with the following structure:

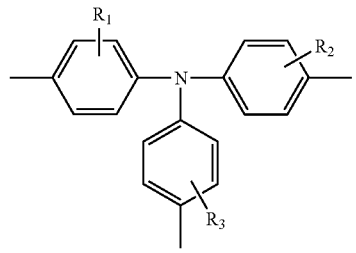

wherein $R_1$, $R_2$, and $R_3$ independently represent hydrogen, an optionally substituted alkyl group, an optionally substituted alkoxy group, or an optionally substituted aryl group and may be same or different from each other.

In the optionally substituted alkyl group, optionally substituted alkoxy group, and optionally substituted aryl group, the substituent group may be substituent groups containing an element such as oxygen, nitrogen, silicon, phosphorus, and sulfur. The aryl group may include a phenyl group and a naphthyl group.

The organic semiconductor material of the invention is characterized by preferably having at least one group among the groups $X^1$, $X^2$, and $X^3$ having an aromatic ring with the following structure;

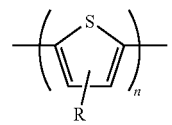

wherein R represents hydrogen, an optionally substituted alkyl group, an optionally substituted alkoxy group, or an optionally substituted aryl group; and n is an integer of 1 to 20.

The organic semiconductor material of the invention may have an asymmetric or symmetric chemical structure with respect to the center of the branching part Y.

The chemical structure of the organic semiconductor material of the invention may have two or more of the branching part Y.

The organic semiconductor material of the invention may be that having the following structure:

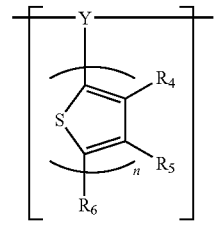

wherein Y represents a branching part of the molecular chain; $R_4$, $R_5$, and $R_6$ independently represent hydrogen, an optionally substituted alkyl group, an optionally substituted alkoxy group, or an optionally substituted aryl group and may be same or different from each other; and n is an integer of 1 to 20.

Further, the organic semiconductor material of the invention may be that having the following structure:

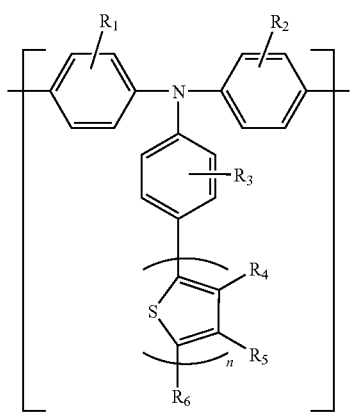

wherein $R_1$ to $R_6$ independently represent hydrogen, an optionally substituted alkyl group, an optionally substituted alkoxy group, or an optionally substituted aryl group and may be same or different from each other; and n is an integer of 1 to 20.

The organic semiconductor material of the invention may be that having a structure defined by the following general formula:

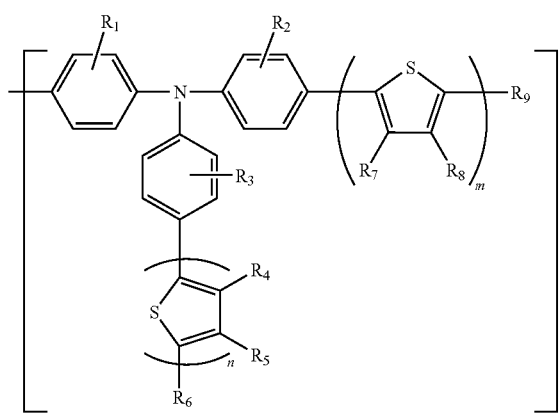

wherein $R_1$ to $R_9$ independently represent hydrogen, an optionally substituted alkyl group, an optionally substituted alkoxy group, or an optionally substituted aryl group and may be same or different from each other; and m and n are an integer of 1 to 20.

Those having the following structure may be the above-mentioned organic semiconductor material having the structure defined by the above general formula.

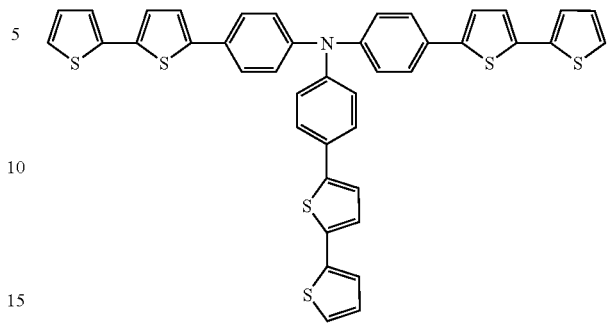

The organic semiconductor material of the invention may be that having a structure defined by the following general formula:

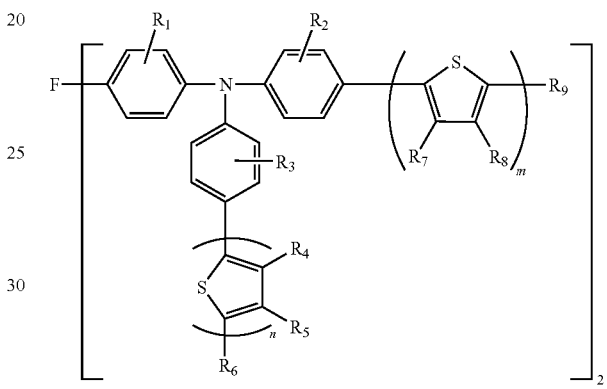

wherein F represents a phenylene derivative, a fluorene derivative, an amine derivative, a phenylamine derivative, or a thiophene derivative; $R_1$ to $R_9$ independently represent hydrogen, an optionally substituted alkyl group, an optionally substituted alkoxy group, or an optionally substituted aryl group and may be same or different from each other; and m and n are an integer of 1 to 20.

F in the above formula may be a unit having conjugated bonds as described above or may be also a non-conjugated unit such as cyclohexane and ether.

Those having the structure defined by the above formula may include the following organic semiconductor materials.

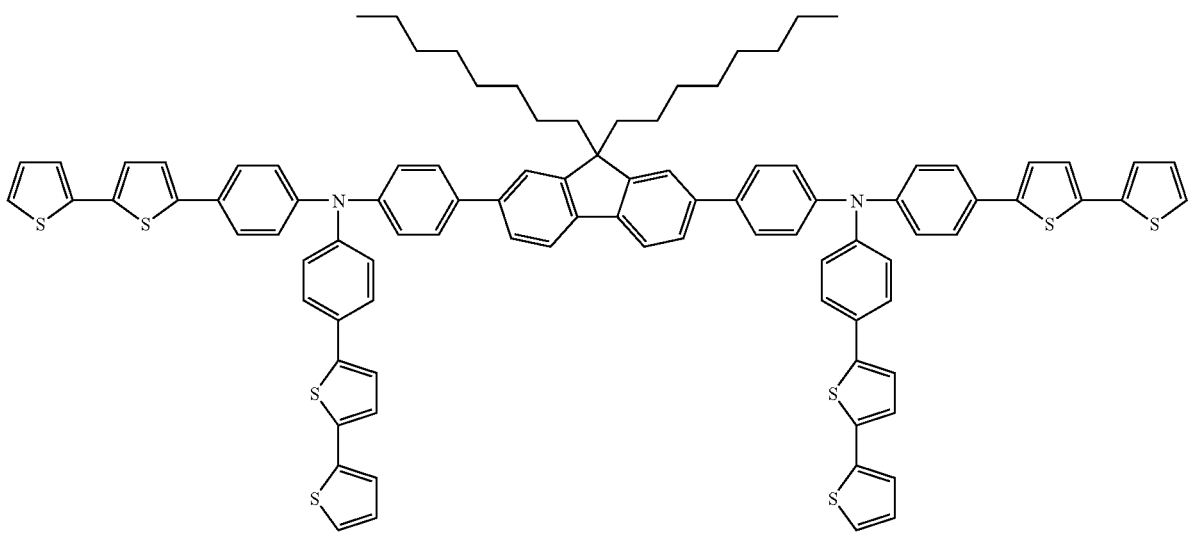

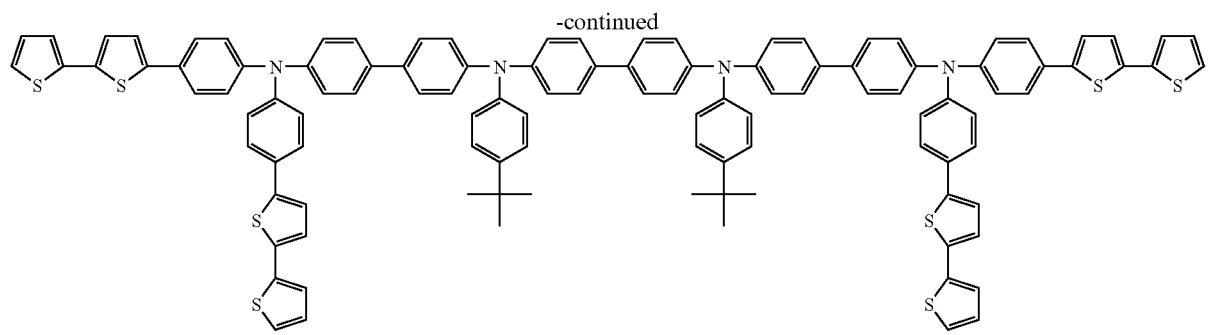

In addition, the organic semiconductor polymer materials shown below are also exemplified.

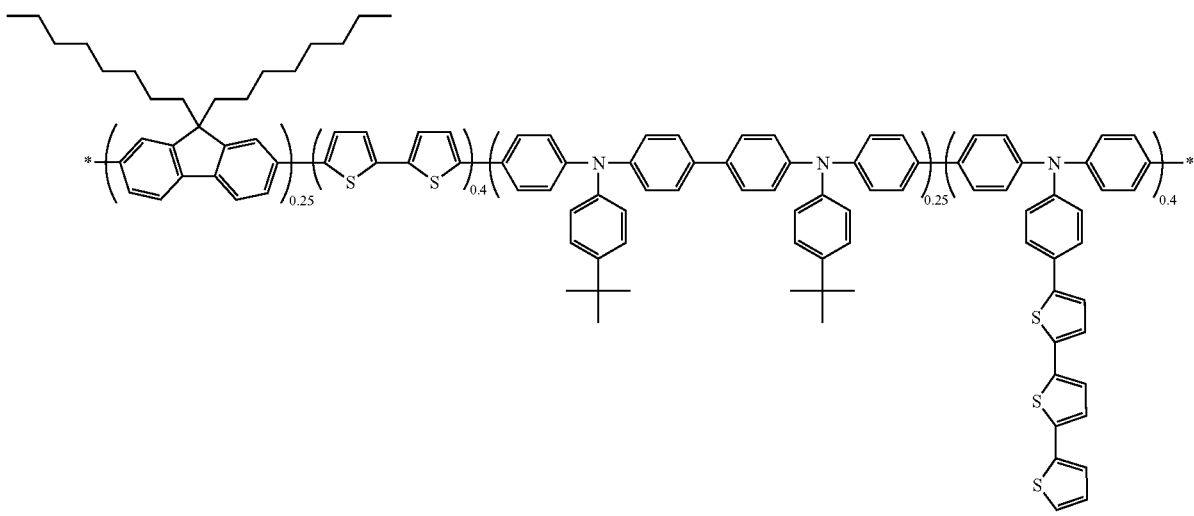

The molecular weight (Mw) in the above-mentioned organic semiconductor polymer materials is preferably in a range of 1,800 to 5,000,000.

The branching part Y in the organic semiconductor material of the invention may be those having the following structure:

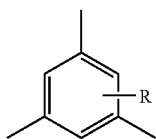

wherein R represents hydrogen, an optionally substituted alkyl group, an optionally substituted alkoxy group, or an optionally substituted aryl group.

Further, the groups X1, X2, and X3 having an aromatic ring in the organic semiconductor material of the invention may be those having the following structure.

In the following structural formulas, $R_1$ to $R_3$ independently represent hydrogen, an optionally substituted alkyl group, an optionally substituted alkoxy group, or an optionally substituted aryl group and may be same or different from each other; and n is an integer of 1 to 20.

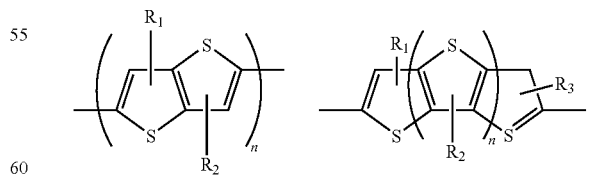

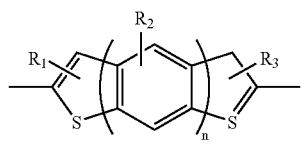

-continued

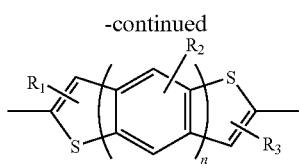

The organic semiconductor element of the invention is characterized by using the above-mentioned organic semiconductor material of the invention.

The organic transistor of the invention is characterized by using the above-mentioned organic semiconductor material of the invention.

The field effect transistor of the invention is a field effect transistor comprising a charge transporting material layer and a gate electrode directly or indirectly contacting the charge transporting material layer and controlling electric current in the charge transporting material layer by applying an electric field between the gate electrode and the charge transporting material layer, wherein the charge transporting material layer is formed using the above-mentioned organic semiconductor material of the invention.

The organic semiconductor material of the invention has high carrier mobility, and when the material is used for the organic semiconductor element, excellent semiconductor properties can be obtained.

DESCRIPTION OF THE PREFERRED EMBODIMENTS

Figure 1:
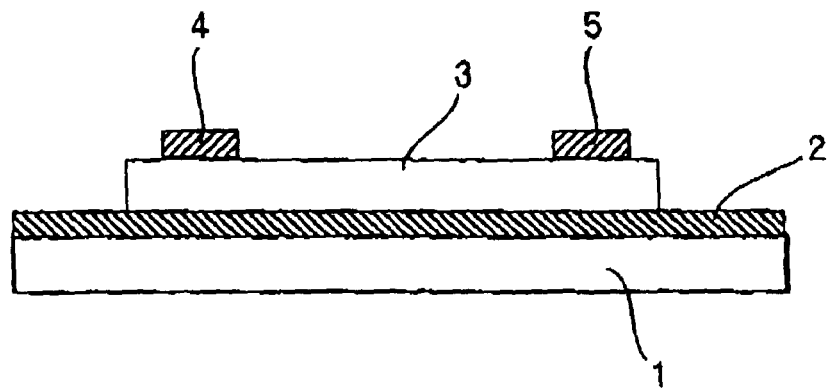
FIG. 1 is a schematic cross-sectional view showing an organic transistor fabricated in Example according to the invention.

Hereinafter, the invention will be described with reference to examples, however the invention should not be limited to the following examples.

<First Aspect of the Invention>

Synthesis Example 1

Synthesis of 4,4'-di(5'''-n-hexyl-tetrathiophene-2-yl)-N,N'-bis[4-(1,1-dimethylethyl)phenyl]-N,N'-bis (1,4-phenylenediyl)-(1,1'-biphenyl)-4,4'-diamine (TPD-n-hexyl-T4)

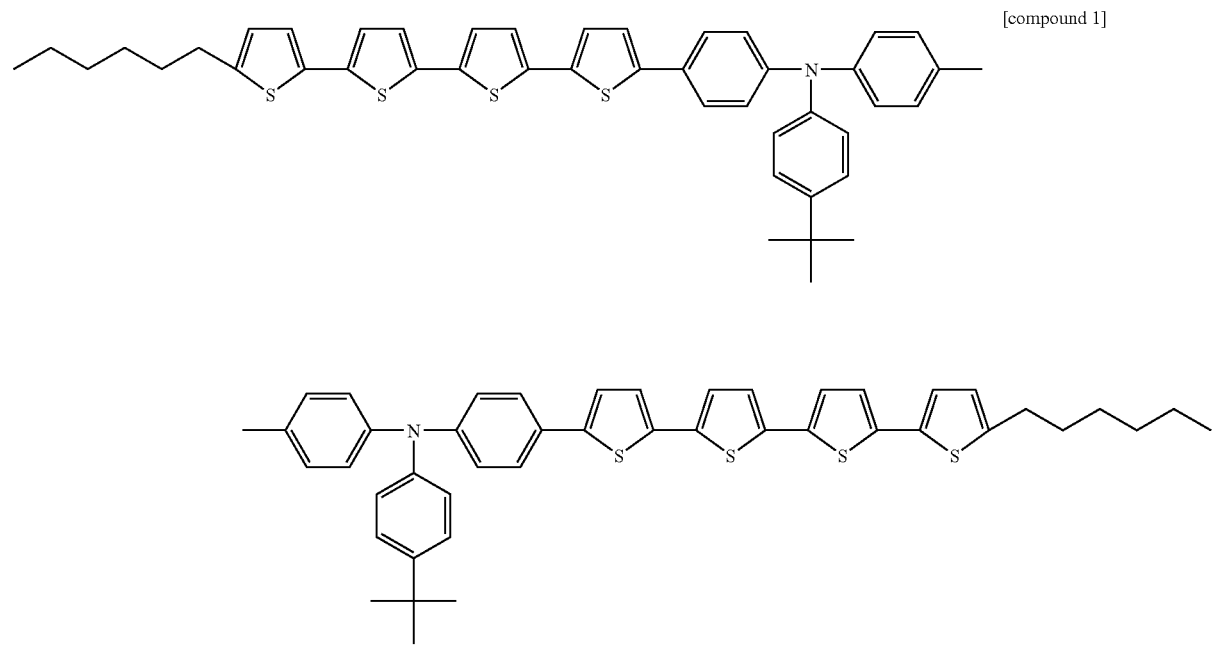

[compound 1]

To a dry air-tight reactor equipped with a mechanical stirrer and connectable to a nitrogen line and a vacuum line are added N,N'-bis[4-(1,1-dimethylethyl)phenyl]-N,N'-bis(1,4-phenylenediyl)-(1,1'-biphenyl)-4,4'-diamine-4,4'-bis(4,4,5,5-tetramethyl)-1,3,2-dioxaborolane (426 mg, 0.5 mmol), 2,5'-dibromo-bithiophene (324 mg, 1 mmol), Suzuki coupling catalyst, toluene 5 ml, tetraethylammonium hydroxide (20 wt %) 8 ml to cause reaction. The reactor is evacuated and purged with nitrogen 3 times and is heated to 95° C. The reaction is kept at 95° C. under nitrogen for 4 hours. Next, 5-(4,4,5,5-tetramethyl-1,3,2-dioxaborolane-2-yl)-5'-N-hexyl-2,2'-bithiophene (395 mg, 1.05 mmol) is added and keep the reaction at 95° C. under nitrogen for further 5 hours.

After cooling the reaction product, the reaction product is added dropwise to 200 ml of methanol to precipitate the product. Next, the product is washed with methanol 3 times. After drying under vacuum, the product is dissolved in 10 ml of chloroform and refined by column chromatography filled with silica gel. After removing some the solvent by a rotary evaporator to condense to proper amount, the product is added dropwise to 200 ml methanol to precipitate the product. The precipitate is washed with methanol 3 times and dried under vacuum. Yellow powder product is obtained as a final product. The yield was about 58%.

Synthesis Example 2

Synthesis of 4,4'-di(5'''-n-hexyl-bithiophene-2-yl)-N,N'-bis[4-(1,1-dimethylethyl)phenyl]-N,N'-bis(1,4-phenylenediyl)-(1,1'-biphenyl)-4,4'-diamine(TPD-n-hexyl-T2)

[compound 2]

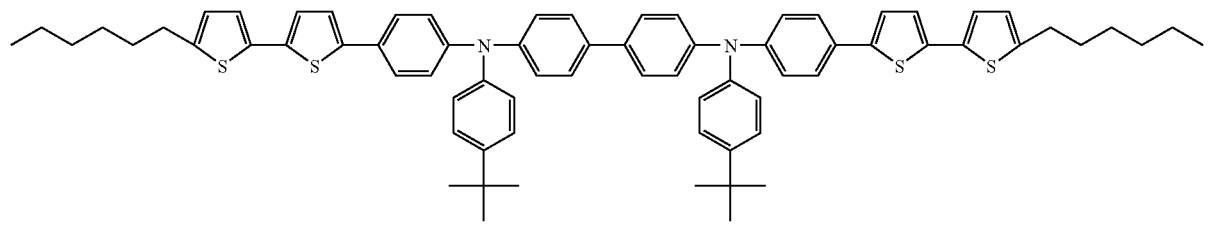

To a dry air-tight reactor equipped with a mechanical stirrer and connectable to a nitrogen line and a vacuum line were added 4,4'-dibromo-N,N'-bis[4-(1,1-dimethylethyl)phenyl]-N,N'-bis(1,4-phenylenediyl)-(1,1'-biphenyl)-4,4'-diamine (379 mg, 0.5 mmol), 5-(4,4,5,5-tetramethyl-1,3,2-dioxaborolane-2-yl)-5'-N-hexyl-2,2'-bithiophene (395 mg, 1.05 mmol), Suzuki coupling catalyst, toluene 5 ml, tetraethylammonium hydroxide (20 wt %) 8 ml to cause reaction. The reactor was evacuated and purged with nitrogen 3 times and was heated to 95° C. The reaction was kept at 95° C. under nitrogen for about 6 hours.

After cooling the reaction product, the reaction product was added dropwise to 200 ml of methanol to precipitate the product. Next, the product was washed with methanol 3 times. After drying under vacuum, the product was dissolved in 10 ml of chloroform and refined by column chromatography filled with silica gel. After removing the solvent by a rotary evaporator to condense to proper amount, the product was added dropwise to 200 ml methanol to precipitate the product. The precipitate was washed with methanol 3 times and dried under vacuum. Yellow powder product was obtained as a final product. The yield was about 58%.

Synthesis Example 3

Synthesis of di(5'''-n-hexyl-bithiophene-2-yl)-tris[N,N'-bis[4-(1,1-dimethylethyl)phenyl]-N,N'-bis(1,4-phenylenediyl)-(1,1'-biphenyl)-4,4'-diamine] (3TPD-n-hexyl-4T2)-n-hexyl-T2)

[compound 3]

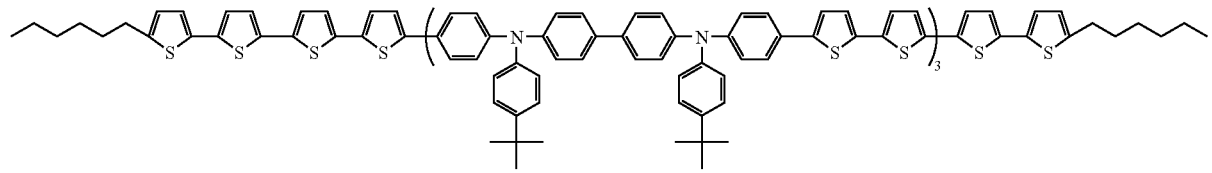

To a dry air-tight reactor equipped with a mechanical stirrer and connectable to a nitrogen line and a vacuum line were added N,N'-bis[4-(1,1-dimethylethyl)phenyl]-N,N'-bis(1,4-phenylenediyl)-(1,1'-biphenyl)-4,4'-diamine-4,4'-bis(4,4,5,5-tetramethyl)-1,3,2-dioxaborolane (426 mg, 0.5 mmol), 2,5'-dibromo-bithiophene (217 mg, 0.67 mmol), Suzuki coupling catalyst, toluene 5 ml, tetraethylammonium hydroxide (20 wt %) 8 ml to cause reaction. The reactor was evacuated and purged with nitrogen 3 times and was heated to 95° C. The reaction was kept at 95° C. under nitrogen for about 4 hours. Next, 5-(4,4,5,5-tetramethyl-1,3,2-dioxaborolane-2-yl)-5'-N-hexyl-2,2'-bithiophene (135 mg, 0.357 mmol) was added and the reaction was kept at 95° C. under nitrogen for further 5 hours.

After cooling the reaction product, the reaction product was added dropwise to 200 ml of methanol to precipitate the product. Next, the product was washed with methanol 3 times. After drying under vacuum, the product was dissolved in 10 ml of chloroform and refined by column chromatography filled with silica gel. After removing the solvent by a rotary evaporator to condense to proper amount, the product was added dropwise to 200 ml methanol to precipitate the product. The precipitate was washed with methanol 3 times and dried under vacuum. Yellow powder product was obtained as a final product. The yield was about 75%.

Synthesis Example 4

Synthesis of poly [(9,9-dioctylfluorene -2,7-diyl)-co-(bithiophene-2,5'-diyl)-co-N,N'-bis[4-(1,1-dimethylethyl)phenyl]-N,N'-bis(1,4-phenylenediyl)-(1,1'-biphenyl)-4,4'-diamine] (PF8-T2(50%)-TPD(25%))

[compound 4]

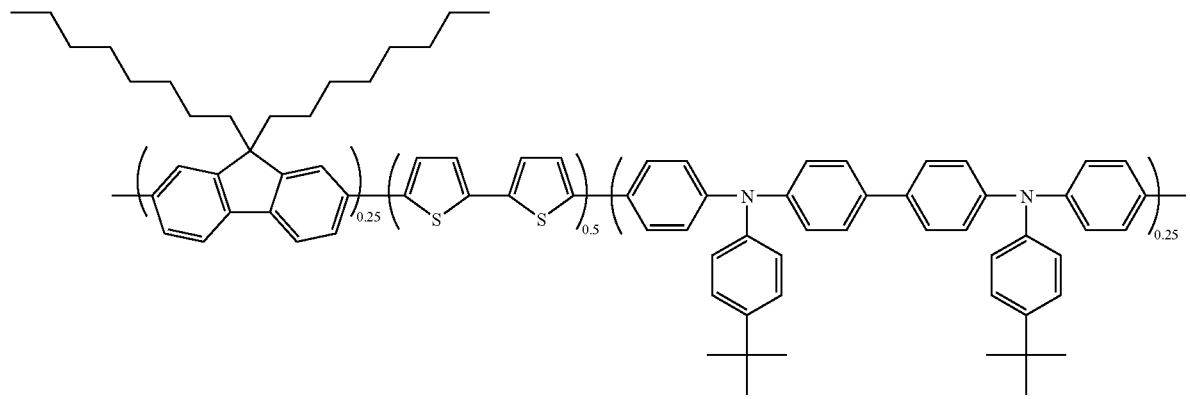

To a dry air-tight reactor equipped with a mechanical stirrer and connectable to a nitrogen line and a vacuum line were added N,N'-bis[4-(1,1-dimethylethyl)phenyl]-N,N'-bis(1,4-phenylenediyl)-(1,1'-biphenyl)-4,4'-diamine-4,4'-bis(4,4,5,5-tetramethyl)-1,3,2-dioxaborolane (213 mg, 0.25 mmol), 9,9-dioctylfluorene-2,7-bis(4,4,5,5-tetramethyl-1,3,2-dioxaborolane (160.5 mg, 0.25 mmol), 2,5'-dibromo-bithiophene (157 mg, 0.5 mmol), Suzuki coupling catalyst, toluene 5 ml, tetraethylammonium hydroxide (20 wt %) 8 ml to cause reaction. The reactor was evacuated and purged with nitrogen 3 times and was heated to 95° C. The reaction was kept at 95° C. under nitrogen for 3 hours. Next, phenyl boronic acid of 61 mg was added and the reaction was kept at 95° C. for about further 2 hours. Thereafter, about 0.12 ml of bromobenzene was added and the reaction was kept at 95° C. under nitrogen further 2 hours.

After cooling the reaction product, the reaction product was added dropwise to 300 ml of methanol to precipitate the product. Next, the product was washed with methanol 3 times. After drying under vacuum, the product was dissolved in 10 ml of toluene and refined by column chromatography filled with silica gel. After removing the solvent by a rotary evaporator to condense to proper amount, the product was added dropwise to 300 ml methanol to precipitate the product. The precipitate was washed with methanol 3 times and dried under vacuum. Brown powder product was obtained as a final product. The yield was about 90%. The number average molecular weight (Mn), the weight average molecular weight (Mw), and Mw/Mn of the obtained polymer were $1.2 \times 10^4$, $3.5 \times 10^4$, and 2.9, respectively.

Synthesis Example 5

Synthesis of poly [(2-decanoxylbenzene-1,4-diyl)-co-(bithiophene-2,5'-diyl)-co-(N,N'-bis[4-(1,1-dimethylethyl)phenyl]-N,N'-bis(1,4-phenylenediyl)-(1,1'-biphenyl)-4,4'-diamine)] (DOP-T2(50%)-TPD(25%))

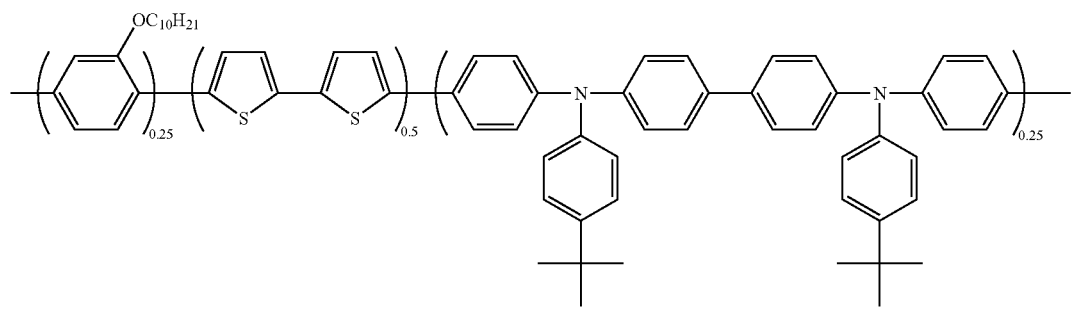

[compound 5]

To a dry air-tight reactor equipped with a mechanical stirrer and connectable to a nitrogen line and a vacuum line were added N,N'-bis[4-(1,1-dimethylethyl)phenyl]-N,N'-bis(1,4-phenylenediyl)-(1,1'-biphenyl)-4,4'-diamine-4,4'-bis(4,4,5,5-tetramethyl)-1,3,2-dioxaborolane (213 mg, 0.25 mmol), 2-decanoxylbenzene-1,4-bis(4,4,5,5-tetramethyl-1,3,2-dioxaborolane (121.4 mg, 0.25 mmol), 2,5'-dibromo-bithiophene (157 mg, 0.5 mmol), Suzuki coupling catalyst, toluene 5 ml, tetraethylammonium hydroxide (20 wt %) 8 ml to cause reaction. The reactor was evacuated and purged with nitrogen 3 times and was heated to 95° C. The reaction was kept at 95° C. under nitrogen for 3 hours. Next, phenyl boronic acid 61 mg was added and the reaction was kept at 95° C. for about further 2 hours. Thereafter, about 0.12 ml of bromobenzene was added and the reaction was kept at 95° C. in nitrogen for further 2 hours.

After cooling the reaction product, the reaction product was added dropwise to 300 ml of methanol to precipitate the product. Next, the product was washed with methanol 3 times. After drying under vacuum, the product was dissolved in 10 ml of toluene and refined by column chromatography filled with silica gel. After removing the solvent by a rotary evaporator to condense to proper amount, the product was added dropwise to 300 ml methanol to precipitate the product. The precipitate was washed with methanol 3 times and dried under vacuum. Brown powder product was obtained as a final product. The yield was about 75%. The number average molecular weight (Mn), the weight average molecular weight (Mw), and Mw/Mn of the obtained polymer were $1.2 \times 10^4$, $2.8 \times 10^4$, and 2.3, respectively.

Synthesis Example 6

Synthesis of di(5'''-n-hexyl-bithiophene-2-yl)-tris[N,N'-bis[4-(1,1-dimethylethyl)phenyl]-N,N'-bis(1,4-phenylenediyl)-(1,1'-biphenyl)-4,4'-diamine-alt-(thiophene-2,5-diyl)] (3TPD-4T)-n-hexyl-T2)

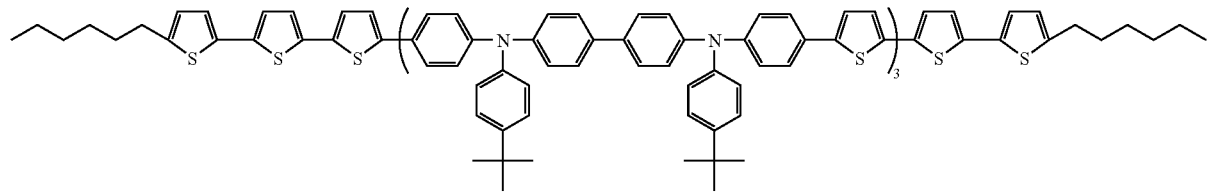

[compound 6]

To a dry air-tight reactor equipped with a mechanical stirrer and connectable to a nitrogen line and a vacuum line were added N,N'-bis[4-(1,1-dimethylethyl)phenyl]-N,N'-bis(1,4-phenylenediyl)-(1,1'-biphenyl)-4,4'-diamine-4,4'-bis(4,4,5,5-tetramethyl)-1,3,2-dioxaborolane (426 mg, 0.5 mmol), 2,5-diiodothiophene (225 mg, 0.67 mmol), Suzuki coupling catalyst, toluene 5 ml, tetraethylammonium hydroxide (20 wt %) 8 ml to cause reaction. The reactor was evacuated and purged with nitrogen 3 times and was heated to 95° C. The reaction was kept at 95° C. under nitrogen for about 4 hours. Next, 5-(4,4,5,5-tetramethyl-1,3,2-dioxaborolane-2-yl)-5'-N-hexyl-2,2'-bithiophene (135 mg, 0.357 mmol) was added and the reaction was kept at 95° C. under nitrogen for further 5 hours.

After cooling the reaction product, the reaction product was added dropwise to 200 ml of methanol to precipitate the product. Next, the product was washed with methanol 3 times. After drying under vacuum, the product was dissolved in 10 ml of chloroform and refined by column chromatography filled with silica gel. After removing the solvent by a rotary evaporator to condense to proper amount, the product was added dropwise to 200 ml methanol to precipitate the product. The precipitate was washed with methanol 3 times and dried under vacuum. Yellow powder product was obtained as a final product. The yield was about 85%.

Synthesis Example 7

Synthesis of di(bitiophene-2-yl)-tris[N,N'-bis[4-(1,1-dimethylethyl)phenyl]-N,N'-bis(1,4-phenylenediyl)-(1,1'-biphenyl)-4,4'-diamine-alt-(thiophene-2,5-diyl)] (3TPD-4T)-T2)

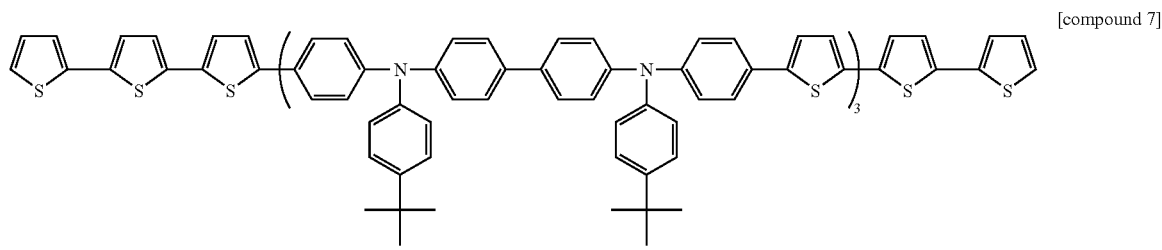

[compound 7]

To a dry air-tight reactor equipped with a mechanical stirrer and connectable to a nitrogen line and a vacuum line were added N,N'-bis[4-(1,1-dimethylethyl)phenyl]-N,N'-bis(1,4-phenylenediyl)-(1,1'-biphenyl)-4,4'-diamine-4,4'-bis (4,4,5,5-tetramethyl)-1,3,2-dioxaborolane (426 mg, 0.5 mmol), 2,5-diiodothiophene (225 mg, 0.67 mmol), Suzuki coupling catalyst, toluene 5 ml, tetraethylammonium hydroxide (20 wt %) 8 ml to cause reaction. The reactor was evacuated and purged with nitrogen 3 times and was heated to 95° C. The reaction was kept at 95° C. under nitrogen for about 4 hours. Next, 5-(4,4,5,5-tetramethyl-1,3,2-dioxaborolane-2-yl)-2,2'-bithiophene (104 mg, 0.357 mmol) was added and the reaction was kept at 95° C. under nitrogen for further 5 hours.

After cooling the reaction product, the reaction product was added dropwise to 200 ml of methanol to precipitate the product. Next, the product was washed with methanol 3 times. After drying under vacuum, the product was dissolved in 10 ml of chloroform and refined by column chromatography filled with silica gel. After removing the solvent by a rotary evaporator to condense to proper amount, the product was added dropwise to 200 ml methanol to precipitate the product. The precipitate was washed with methanol 3 times and dried under vacuum. Yellow powder product was obtained as a final product. The yield was about 42%.

Synthesis Example 8

Synthesis of poly[(9,9-dioctylfluorene-2,7-diyl)-co-(thiophene-2,5'-diyl)-co-N,N'-bis[4-(1,1-dimethylethyl)phenyl]-N,N'-bis(1,4-phenylenediyl)-(1,1'-biphenyl)-4,4'-diamine)] (PF8-T(50%)-TPD(25%))

[compound 8]

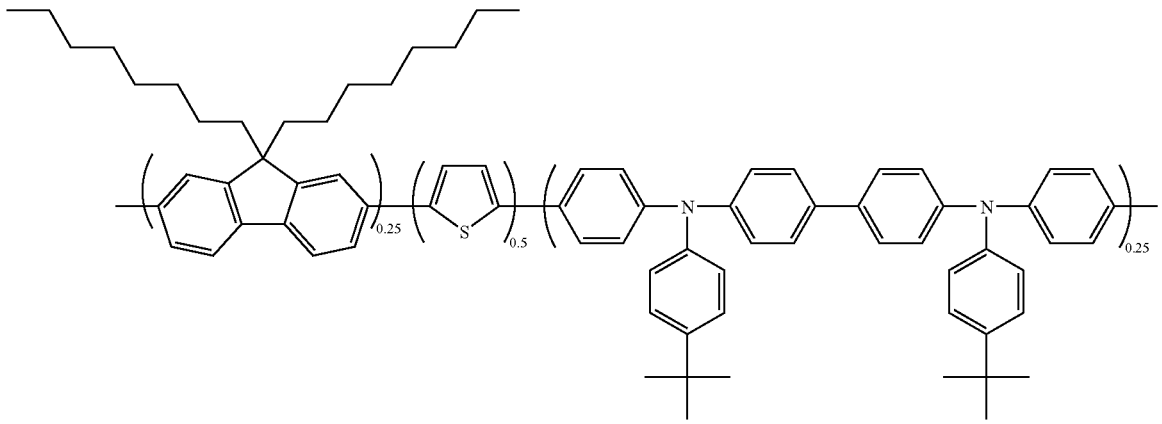

To a dry air-tight reactor equipped with a mechanical stirrer and connectable to a nitrogen line and a vacuum line were added N,N'-bis[4-(1,1-dimethylethyl)phenyl]-N,N'-bis(1,4-phenylenediyl)-(1,1'-biphenyl)-4,4'-diamine-4,4'-bis(4,4,5,5-tetramethyl)-1,3,2-dioxaborolane (213 mg, 0.25 mmol), 9,9-dioctylfluorene-2,7-bis(4,4,5,5-tetramethyl-1,3,2-dioxaborolane (160.5 mg, 0.25 mmol), 2,5'-diiodothiophene (168 mg, 0.5 mmol), Suzuki coupling catalyst, toluene 5 ml, tetraethylammonium hydroxide (20 wt %) 8 ml to cause reaction. The reactor was evacuated and purged with nitrogen 3 times and was heated to 95° C. The reaction was kept at 95° C. under nitrogen for about 3 hours. Next, phenyl boronic acid 61 mg was added and the reaction was kept at 95° C. for further 2 hours. Thereafter, about 0.12 ml of bromobenzene was added and the reaction was kept at 95° C. under nitrogen for further 2 hours.

After cooling the reaction product, the reaction product was added dropwise to 300 ml of methanol to precipitate the product. Next, the product was washed with methanol 3 times. After drying under vacuum, the product was dissolved in 10 ml of toluene and refined by column chromatography filled with silica gel. After removing the solvent by a rotary evaporator to condense to proper amount, the product was added dropwise to 300 ml methanol to precipitate the product. The precipitate was washed with methanol 3 times and dried under vacuum. Yellow fiber product was obtained as a final product. The yield was about 90%. The number average molecular weight (Mn), the weight average molecular weight (Mw), and Mw/Mn of the obtained polymer were $3.2 \times 10^4$, $7.5 \times 10^4$, and 2.34, respectively.

Synthesis Example 9

Synthesis of poly[(2-decanoxylbenzene-1,4-diyl)-co-(thiophene-2,5'-diyl)-co-(N,N'-bis[4-(1,1-dimethylethyl)phenyl]-N,N'-bis(1,4-phenylenediyl)-(1,1'-biphenyl)-4,4'-diamine)] (PF8-T(50%)-TPD(25%))

[compound 9]

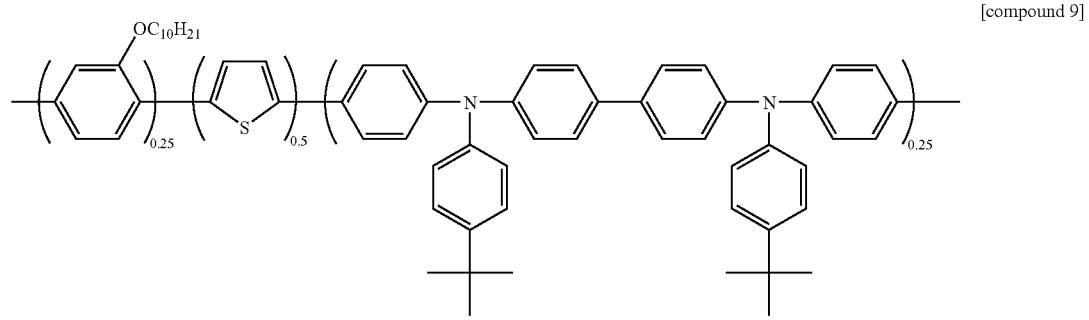

To a dry air-tight reactor equipped with a mechanical stirrer and connectable to a nitrogen line and a vacuum line were added N,N'-bis[4-(1,1-dimethylethyl)phenyl]-N,N'-bis(1,4-phenylenediyl)-(1,1'-biphenyl)-4,4'-diamine-4,4'-bis(4,4,5,5-tetramethyl)-1,3,2-dioxaborolane (213 mg, 0.25 mmol), 2-decanoxylbenzene-1,4-bis(4,4,5,5-tetramethyl-1,3,2-dioxaborolane (121.4 mg, 0.25 mmol), 2,5'-diiodothiophene (168 mg, 0.5 mmol), Suzuki coupling catalyst, toluene 5 ml, tetraethylammonium hydroxide (20 wt %) 8 ml to cause reaction. The reactor was evacuated and purged with nitrogen 3 times and was heated to 95° C. The reaction was kept at 95° C. under nitrogen for about 3 hours. Next, phenyl boronic acid 61 mg was added and the reaction was kept at 95° C. for further 2 hours. Thereafter, about 0.12 ml of bromobenzene was added and the reaction was kept at 95° C. under nitrogen for further 2 hours.

After cooling the reaction product, the reaction product was added dropwise to 300 ml of methanol to precipitate the product. Next, the product was washed with methanol 3 times. After drying under vacuum, the product was dissolved in 10 ml of toluene and refined by column chromatography filled with silica gel. After removing the solvent by a rotary evaporator to condense to proper amount, the product was added dropwise to 300 ml methanol to precipitate the product. The precipitate was washed with methanol 3 times and dried under vacuum. Yellow powder product was obtained as a final product. The yield was about 81%. The number average molecular weight (Mn), the weight average molecular weight (Mw), and Mw/Mn of the obtained polymer were $1.8 \times 10^4$, $4.1 \times 10^4$, and 2.44, respectively.

Synthesis Example 10

Synthesis of 4,4'-di(5''''-n-hexyl-pentathiophene-2-yl)-N,N'-bis [4-(1,1-dimethylethyl)phenyl]-N,N'-bis (1,4-phenylenediyl)-(1,1'-biphenyl)-4,4'-diamine (TPD-n-hexyl-T5)

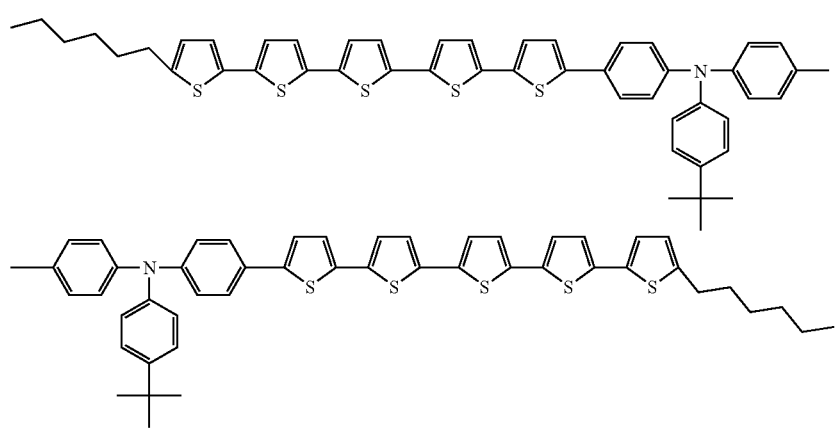

[compound 10]

To a dry air-tight reactor equipped with a mechanical stirrer and connectable to a nitrogen line and a vacuum line were added 4,4'-dibromo-N,N'-bis[4-(1,1-dimethylethyl)phenyl]-N,N'-bis(1,4-phenylenediyl)-(1,1'-biphenyl)-4,4'-diamine (379 mg, 0.5 mmol), 5,5'-di(4,4,5,5-tetramethyl-1,3,2-dioxaborolane-2-yl)-2,2'-bithiophene (418 mg, 1 mmol), Suzuki coupling catalyst, toluene 5 ml, tetraethylammonium hydroxide (20 wt %) 8 ml to cause reaction. The reactor was evacuated and purged with nitrogen 3 times and was heated to 95° C. The reaction was kept at 95° C. under nitrogen for about 3 hours. Next, 2,5-diiodo-thiophene (336 mg, 1 mmol) was added and the reaction was kept at 95° C. for further 3 hours. Further, 5-(4,4,5,5-tetramethyl-1,3,2-dioxaborolane-2-yl)-5'-N-hexyl-2,2'-bithiophene (395 mg, 1.05 mmol) was added and the reaction was kept at 95° C. under nitrogen for further 4 hours.

After cooling the reaction product, the reaction product was added dropwise to 200 ml of methanol to precipitate the product. Next, the product was washed with methanol 3 times. After drying under vacuum, the product was dissolved in 10 ml of chloroform and refined by column chromatography filled with silica gel. After removing the solvent by a rotary evaporator to condense to proper amount, the product was added dropwise to 200 ml methanol to precipitate the product. The precipitate was washed with methanol 3 times and dried under vacuum. Yellow powder product was obtained as a final product. The yield was about 43%.

Synthesis Example 11

Synthesis of 4,4'-di(5''''-n-hexyl-pentathiophene-2-yl)-triphenylamine

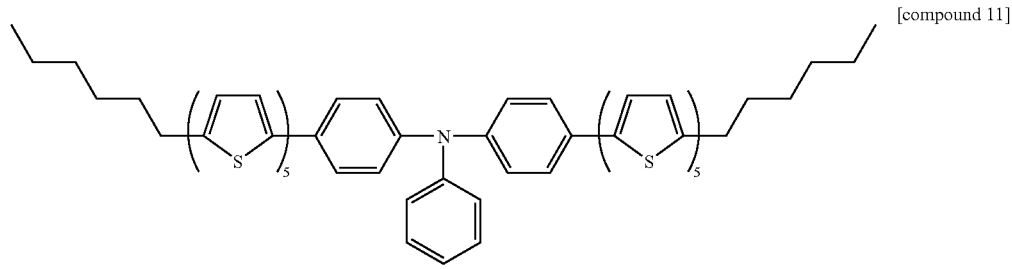

[compound 11]

To a dry air-tight reactor equipped with a mechanical stirrer and connectable to a nitrogen line and a vacuum line were added 4,4'-dibromo-triphenylamine (202 mg, 0.5 mmol), 5,5'-di(4,4,5,5-tetramethyl-1,3,2-dioxaborolane-2-yl)-2,2'-bithiophene (418 mg, 1 mmol), Suzuki coupling catalyst, toluene 5 ml, tetraethylammonium hydroxide (20 wt %) 8 ml to cause reaction. The reactor was evacuated and purged with nitrogen 3 times and was heated to 95° C. The reaction was kept at 95° C. under nitrogen for about 3 hours. Next, 2,5,diiodothiophene (336 mg, 1 mmol) was added and the reaction was kept at 95° C. for further 3 hours. Further, 5-(4,4,5,5-tetramethyl-1,3,2-dioxaborolane-2-yl)-5'-n-hexyl-2,2'-bithiophene (395 mg, 1.05 mmol) was added and the reaction was kept at 95° C. under nitrogen for further 4 hours.

After cooling the reaction product, the reaction product was added dropwise to 200 ml of methanol to precipitate the product. Next, the product was washed with methanol 3 times. After drying under vacuum, the product was dissolved in 10 ml of chloroform and refined by column chromatography filled with silica gel. After removing the solvent by a rotary evaporator to condense to proper amount, the product was added dropwise to 200 ml methanol to precipitate the product. The precipitate was washed with methanol 3 times and dried under vacuum. Brown powder product was obtained as a final product. The yield was about 20%.

Synthesis Example 12

Synthesis of 4,4'-di(5''''-n-hexyl-pentathiophene-2-yl)-N,N'-diphenyl-N,N'-bis(1,4-phenylenediyl)-(1,1'-biphenyl)-4,4'-diamine

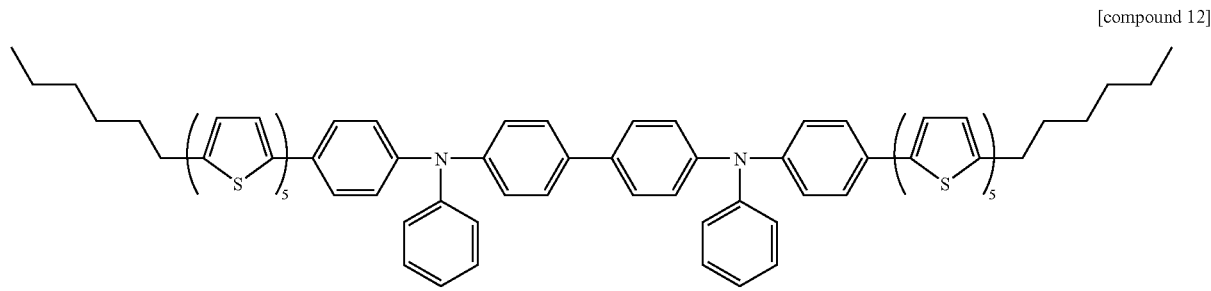

[compound 12]

To a dry air-tight reactor equipped with a mechanical stirrer and connectable to a nitrogen line and a vacuum line were added 4,4'-dibromo-N,N'-diphenyl-N,N'-bis(1,4-phenylenediyl)-(1,1'-biphenyl)-4,4'-diamine (323 mg, 0.5 mmol), 5,5'-di(4,4,5,5-tetramethyl-1,3,2-dioxaborolane-2-yl)-2,2'-bithiophene (418 mg, 1 mmol), Suzuki coupling catalyst, toluene 5 ml, tetraethylammonium hydroxide (20 wt %) 8 ml to cause reaction. The reactor was evacuated and purged with nitrogen 3 times and was heated to 95° C. The reaction was kept at 95° C. under nitrogen for about 3 hours. Next, 2,5-diiodothionene (336 mg, 1 mmol) was added and the reaction was kept at 95° C. for further 3 hours. Further, 5-(4,4,5,5-tetramethyl-1,3,2-dioxaborolane-2-yl)-5'-n-hexyl-2,2'-bithiophene (395 mg, 1.05 mmol) was added and the reaction was kept at 95° C. under nitrogen for further 4 hours.

After cooling the reaction product, the reaction product was added dropwise to 200 ml of methanol to precipitate the product. Next, the product was washed with methanol 3 times. After drying under vacuum, the product was dissolved in 10 ml of chloroform and refined by column chromatography filled with silica gel. After removing the solvent by a rotary evaporator to condense to proper amount, the product was added dropwise to 200 ml methanol to precipitate the product. The precipitate was washed with methanol 3 times and dried under vacuum. Brown powder product was obtained as a final product. The yield was about 25%.

Synthesis Example 13

Synthesis of poly[(bithiophene-2,5'-diyl)-co-(N,N'-bis[4-(1,1-dimethylethyl)phenyl]-N,N'-bis(1,4-phenylenediyl)-(1,1'-biphenyl)-4,4'-diamine)]

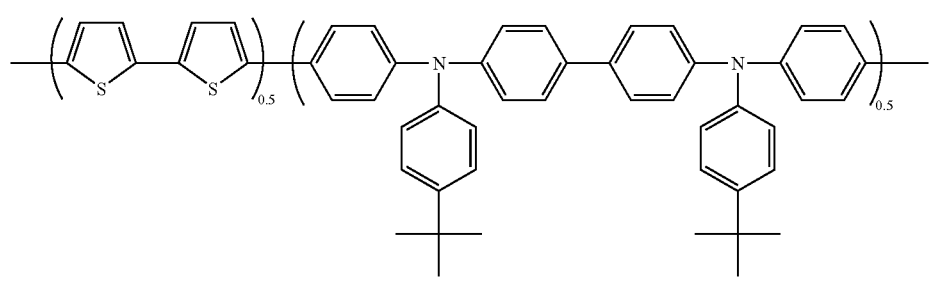

[compound 13]

To a dry air-tight reactor equipped with a mechanical stirrer and connectable to a nitrogen line and a vacuum line were added N,N'-bis[4-(1,1-dimethylethyl)phenyl]-N,N'-bis(1,4-phenylenediyl)-(1,1'-biphenyl)-4,4'-diamine-4,4'-bis(4,4,5,5-tetramethyl)-1,3,2-dioxaborolane (426 mg, 0.5 mmol), 2,5'-dibromo-bithiophene (157 mg, 0.5 mmol), Suzuki coupling catalyst, toluene 5 ml, tetraethylammonium hydroxide (20 wt %) 8 ml to cause reaction. The reactor was evacuated and purged with nitrogen 3 times and was heated to 95° C. The reaction was kept at 95° C. under nitrogen for about 3 hours. Next, phenyl boronic acid 61 mg was added and the reaction was kept at 95° C. for further 2 hours. Thereafter, about 0.12 ml of bromobenzene was added and the reaction was kept at 95° C. under nitrogen for further 2 hours.

After cooling the reaction product, the reaction product was added dropwise to 300 ml of methanol to precipitate the product. Next, the product was washed with methanol 3 times. After drying under vacuum, the product was dissolved in 10 ml of toluene and refined by column chromatography filled with silica gel. After removing the solvent by a rotary evaporator to condense to proper amount, the product was added dropwise to 300 ml methanol to precipitate the product. The precipitate was washed with methanol 3 times and dried under vacuum. Brown powder product was obtained as a final product. The yield was about 75%. The number average molecular weight (Mn), the weight average molecular weight (Mw), and Mw/Mn of the obtained polymer were 9600, 16700, and 1.74, respectively.

Fabrication of Organic Transistor: Examples 1 to 9 and Comparative Example 1

MOS type field effect transistors were fabricated using the organic semiconductor materials synthesized above.

FIG. 1 is a schematic cross-sectional view showing the structure of a fabricated MOS type field effect transistor. As shown in FIG. 1, an insulating layer 2 was formed on a silicon wafer 1, an organic semiconductor film 3 was formed on the insulating layer 2, and a source electrode 4 and a drain electrode 5 at a prescribed distance between the electrodes were formed on the organic semiconductor film 3.

Figure 2:
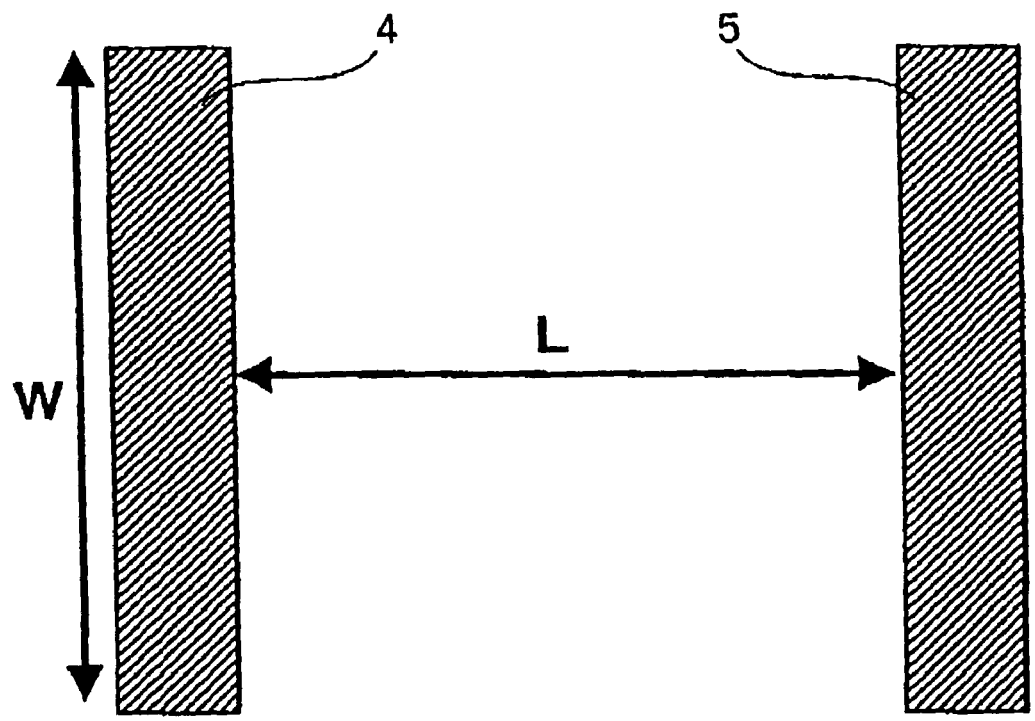
FIG. 2 is a plane view of a source electrode and a drain electrode in the organic transistor shown in FIG. 1.

FIG. 2 is a plane view showing the source electrode 4 and the drain electrode 5. As shown in FIG. 2, the distance between the source electrode 4 and the drain electrode 5 is defined as the channel length L, and each width of the source electrode 4 and the drain electrode 5 is defined as the channel width W.

In the organic transistor shown in FIG. 1, the n-doped silicon wafer 1 is used as the gate electrode. The insulating layer 2 of silicon dioxide with a thickness of 100 nm is formed on the silicon wafer 1. The silicon wafer 1 was washed with 2-propanol, acetone, ion-exchanged water, and methanol in this order by ultrasonic washing and successively surface-cleaned with ultraviolet and ozone treatment before it was used. An organic semiconductor film 3 is formed on the insulating layer 2.

The organic semiconductor film 3 was formed as follows. An organic semiconductor material was dissolved in an organic solvent to produce a solution and the solution was applied to the surface of the insulating layer 2 by spin-coating and baked at 80° C. for 1 hour under reduced pressure in a vacuum oven to remove the organic solvent. Accordingly, the organic semiconductor film 3 with a thickness of 100 nm to 150 nm was formed.

The source electrode 4 and the drain electrode 5 of gold were formed on the organic semiconductor film 3 by vacuum deposition.

The transistor characteristics among three terminals; the gate electrode of the silicon wafer 1, the source electrode 4, and the drain electrode 5; was evaluated at a room temperature (about 27° C.) by 4156C precision semiconductor parameter analyzer manufactured by Agilent Technologies.

Example 1

The organic semiconductor film 3 was formed using the compound 1 and the characteristics of the obtained organic transistor was evaluated as described above. The channel length L was 0.1 mm and the channel width W was 1 mm.

Figure 3:
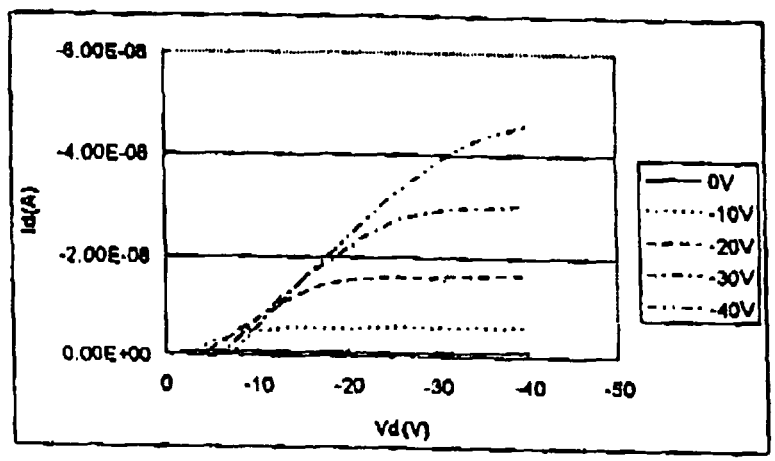
FIG. 3 is a drawing showing V-I characteristic of the organic transistor fabricated in Example 1.

FIG. 3 is a drawing showing the V-I characteristic. The on/off ratio was 57 and the mobility was $1.44 \times 10^{-4}$ cm$^2$/VS and thus good transistor characteristics were obtained.

Example 2

The organic semiconductor film 3 was formed using the compound 2 and the characteristics of the obtained organic transistor was evaluated as described above. The channel length L was 0.1 mm and the channel width W was 1 mm.

Figure 4:
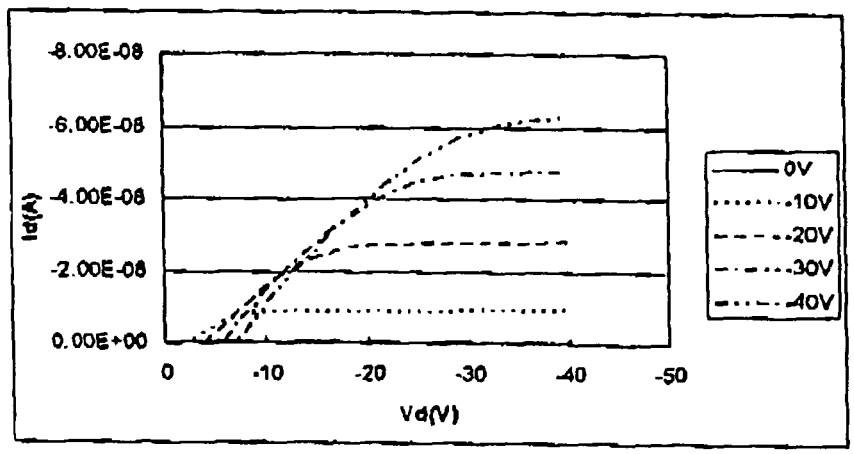
FIG. 4 is a drawing showing V-I characteristic of the organic transistor fabricated in Example 2.

FIG. 4 is a drawing showing the V-I characteristic. The on/off ratio was 167 and the mobility was $4.7 \times 10^{-4}$ cm$^2$/VS and thus good transistor characteristics were obtained.

Example 3

The organic semiconductor film 3 was formed using the compound 3 and the characteristics of the obtained organic transistor was evaluated as described above. The channel length L was 0.07 mm and the channel width W was 1 mm.

Figure 5:
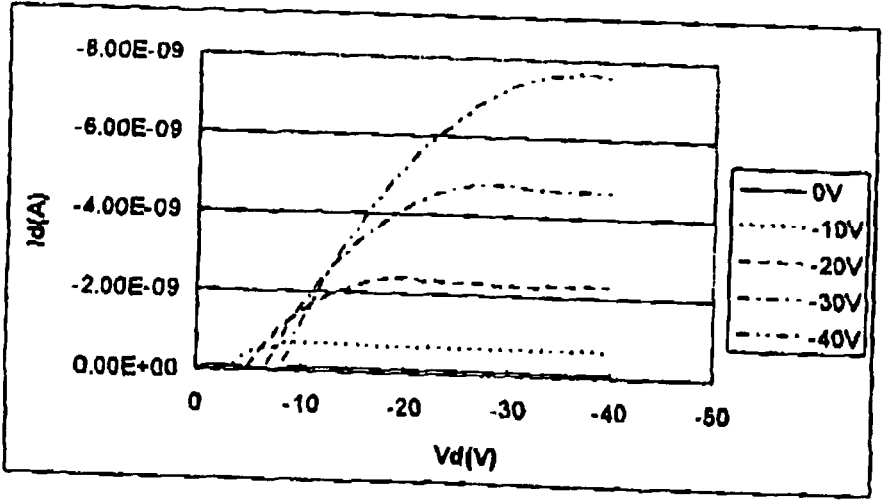
FIG. 5 is a drawing showing V-I characteristic of the organic transistor fabricated in Example 3.

FIG. 5 is a drawing showing the V-I characteristic. The on/off ratio was 87 and the mobility was $1.6 \times 10^{-4}$ cm$^2$/VS and thus good transistor characteristics were obtained.

Example 4

The organic semiconductor film 3 was formed using the compound 4 and the characteristics of the obtained organic transistor was evaluated as described above. The channel length L was 0.2 mm and the channel width W was 1 mm.

Figure 6:
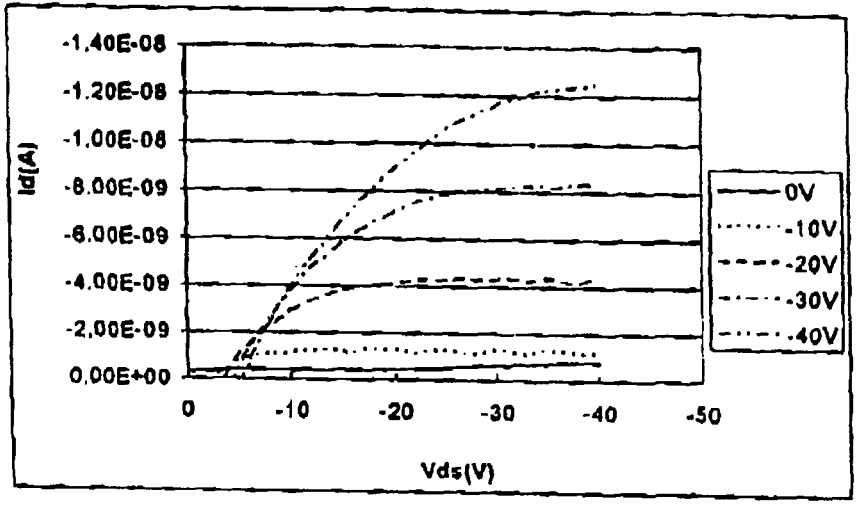
FIG. 6 is a drawing showing V-I characteristic of the organic transistor fabricated in Example 4.

FIG. 6 is a drawing showing the V-I characteristic. The on/off ratio was 16 and the mobility was $1.04 \times 10^{-4}$ cm$^2$/VS and thus good transistor characteristics were obtained.

Comparative Example 1

An organic transistor was fabricated in the same manner as described above, except that P3HT defined by the following structural formula was used. The channel length L was 0.2 mm and the channel width W was 1 mm.

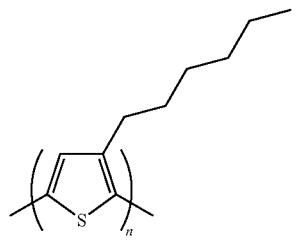

P3HT

Figure 7:
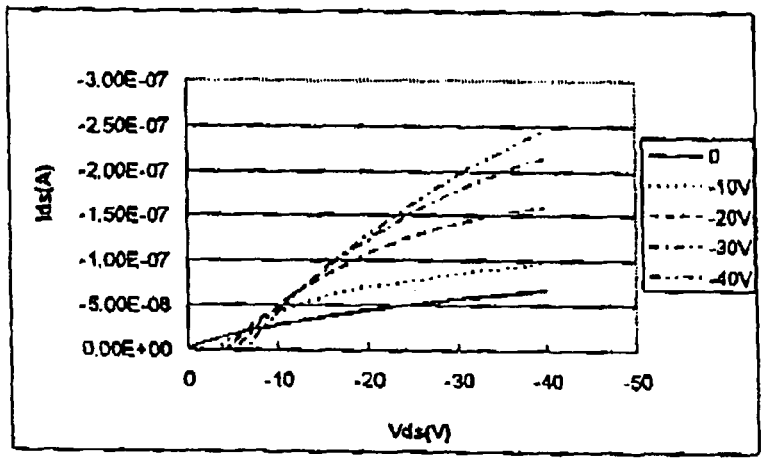
FIG. 7 is a drawing showing V-I characteristic of the organic transistor fabricated in Comparative Example 1.

FIG. 7 is a drawing showing the V-I characteristic. The on/off ratio was as low as 3.6 and the mobility was $7.4 \times 10^{-4}$ cm$^2$/VS.

Example 5

The organic semiconductor films 3 were formed using the compounds 5 to 9 and organic transistors were fabricated. The results are shown in Table 1.

TABLE 1

| Compound | Channel Length L (mm) | Channel Width W (mm) | On/Off Ratio | Mobility (cm$^2$/VS) |
|---|---|---|---|---|
| Compound 5 | 0.2 | 1 | 6 | $4.6 \times 10^{-5}$ |
| Compound 6 | 0.2 | 1 | 8 | $4.6 \times 10^{-5}$ |
| Compound 7 | 0.05 | 1 | 49 | $2.88 \times 10^{-4}$ |
| Compound 8 | 0.05 | 1 | 9 | $2.6 \times 10^{-5}$ |
| Compound 9 | 0.3 | 1 | 6 | $1.4 \times 10^{-5}$ |

Example 6

The organic semiconductor film 3 was formed using the compound 10 and the characteristics of the obtained organic transistor was evaluated as described above. The channel length L was 0.2 mm and the channel width W was 1 mm.

Figure 8:
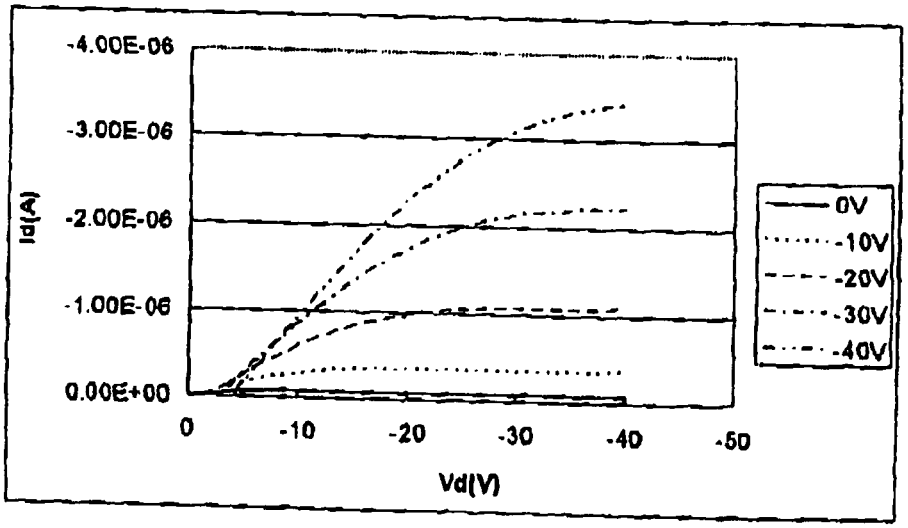
FIG. 8 is a drawing showing V-I characteristic of the organic transistor fabricated in Example 6.

FIG. 8 is a drawing showing the V-I characteristic. The on/off ratio was 44 and the mobility was $2.88 \times 10^{-2}$ cm$^2$/VS and thus good transistor characteristics were obtained.

Example 7

The organic semiconductor film 3 was formed using the compound 11 and the characteristics of the obtained organic transistor was evaluated as described above. The channel length L was 0.2 mm and the channel width W was 10 mm.

Figure 9:
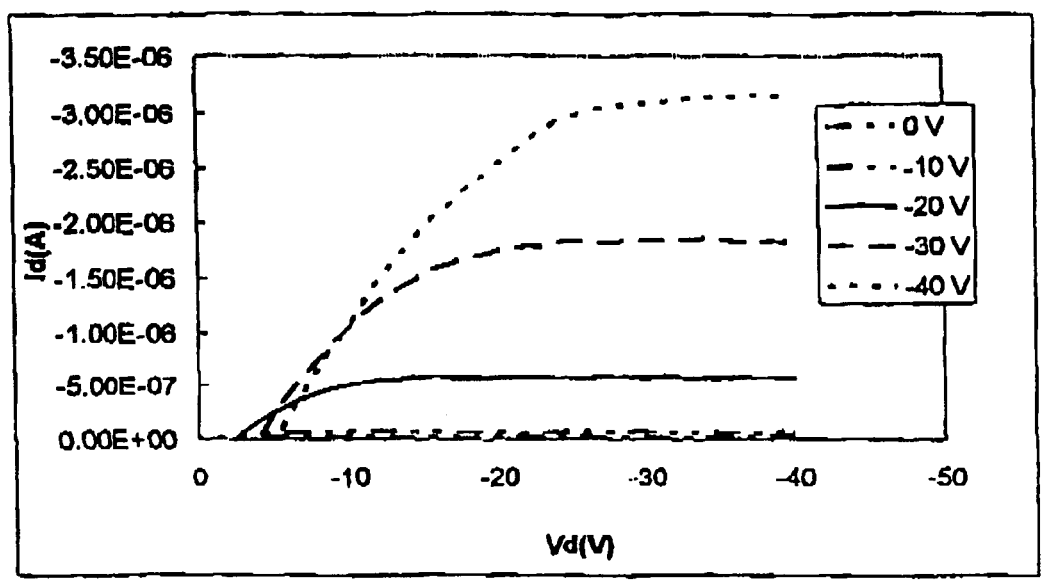
FIG. 9 is a drawing showing V-I characteristic of the organic transistor fabricated in Example 7.

FIG. 9 is a drawing showing the V-I characteristic. The on/off ratio was 246 and the mobility was $5.65 \times 10^{-3}$ cm$^2$/VS and thus good transistor characteristics were obtained.

Example 8

The organic semiconductor film 3 was formed using the compound 12 and the characteristics of the obtained organic transistor was evaluated as described above. The channel length L was 0.05 mm and the channel width W was 1 mm.

Figure 10:
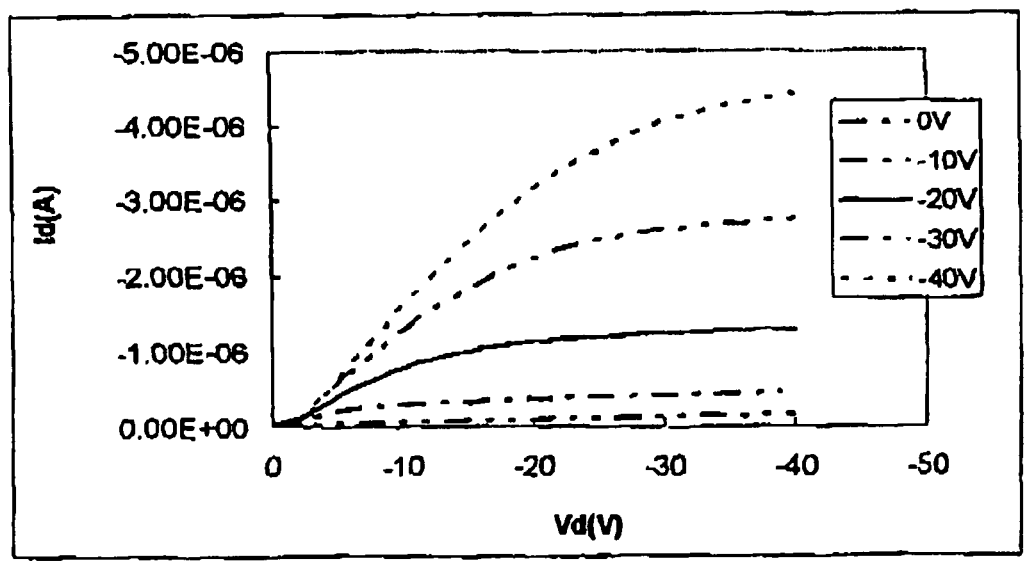
FIG. 10 is a drawing showing V-I characteristic of the organic transistor fabricated in Example 8.

FIG. 10 is a drawing showing the V-I characteristic. The on/off ratio was 108 and the mobility was $6.67 \times 10^{-3}$ cm$^2$/VS and thus good transistor characteristics were obtained.

Example 9

The organic semiconductor film 3 was formed using the compound 13 and the characteristics of the obtained organic transistor was evaluated as described above. The channel length L was 0.2 mm and the channel width W was 1 mm.

Figure 11:
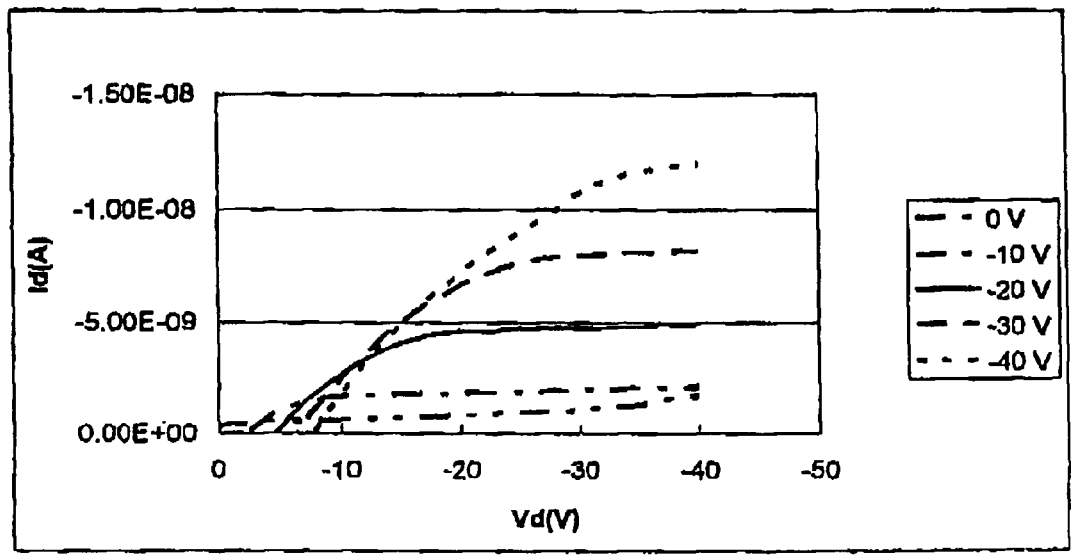
FIG. 11 is a drawing showing V-I characteristic of the organic transistor fabricated in Example 9.

FIG. 11 is a drawing showing the V-I characteristic. The on/off ratio was 6.9 and the mobility was $4.6 \times 10^{-5}$ cm$^2$/VS and thus good transistor characteristics were obtained.

Accordingly, the organic transistors comprising the organic semiconductor films formed using the organic semiconductor materials of the invention had good transistor characteristics. Consequently, the organic semiconductor material according to the invention has a high carrier mobility and suitable for giving good transistor characteristics if being used for the organic transistor.

<Second Aspect of the Invention>

Synthesis Example 14

Synthesis of tris[4-(2,2'-bithiophene-5-yl)phenyl]amine (TPA-3T2)

[compound 14]

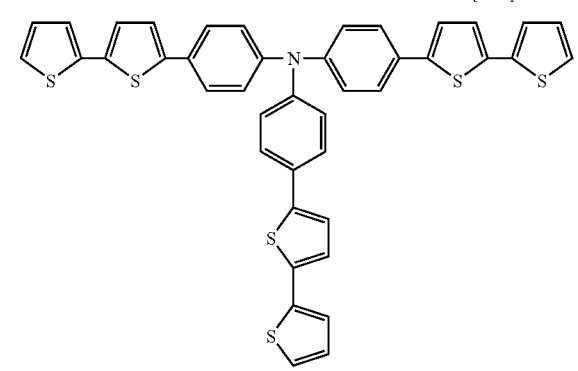

To a dry air-tight reactor equipped with a mechanical stirrer and connectable to a nitrogen line and a vacuum line were added tris(4-bromophenyldiamine)amine (241 mg, 0.5 mmol), 5-(4,4,5,5-tetramethyl-1,3,2-dioxaborolane-2-yl)-2,2'-bithiophene (460 mg, 1.575 mmol), Suzuki coupling catalyst, toluene 5 ml, tetraethylammonium hydroxide (20 wt %) 8 ml to cause reaction. The reactor was evacuated and purged with nitrogen 3 times and was heated to 95° C. The reaction was kept at 95° C. under nitrogen for about 8 hours.

After cooling the reaction product, the reaction product was added dropwise to 200 ml of methanol to precipitate the product. Next, the product was washed with methanol 3 times. After drying under vacuum, the product was dissolved in 10 ml of chloroform and refined by column chromatography filled with silica gel. After removing the solvent by a rotary evaporator to condense to proper amount, the product was added dropwise to 200 ml methanol to precipitate the product. The precipitate was washed with methanol 3 times and dried under vacuum. Yellow powder product was obtained as a final product. The yield was about 12%.

Synthesis Example 15

Synthesis of bis[bis[(5-bithiophene-2-yl]-1,4-phenylenediyl]amino-1,4-phenylenediyl]-9,9-dioctylfluorene-2,7-diyl(F8-TPA-4T2)

[compound 15]

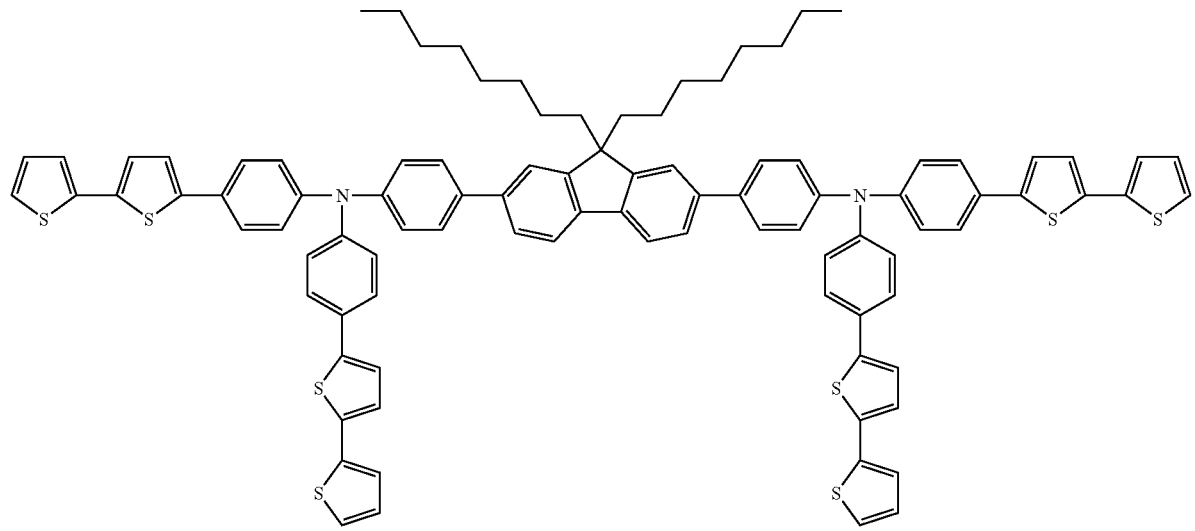

To a dry air-tight reactor equipped with a mechanical stirrer and connectable to a nitrogen line and a vacuum line were added tris(4-bromophenyldiamine)amine (482 mg, 1 mmol), 9,9-dioctyl-2,7-dibromofluorene (321 mg, 0.5 mmol), Suzuki coupling catalyst, toluene 5 ml, tetraethylammonium hydroxide (20 wt %) 8 ml to cause reaction. The reactor was evacuated and purged with nitrogen 3 times and was heated to 95° C. The reaction was kept at 95° C. under nitrogen for about 4.5 hours. Next, 5-(4,4,5,5-tetramethyl-1,3,2-dioxaborolane-2-yl)-2,2'-bithiophene (614 mg, 2.1 mmol) was added and the reaction was kept at 95° C. under nitrogen for further 5 hours.

After cooling the reaction product, the reaction product was added dropwise to 200 ml of methanol to precipitate the product. Next, the product was washed with methanol 3 times. After drying under vacuum, the product was dissolved in 10 ml of chloroform and refined by column chromatography filled with silica gel. After removing the solvent by a rotary evaporator to condense to proper amount, the product was added dropwise to 200 ml methanol to precipitate the product. The precipitate was washed with methanol 3 times and dried under vacuum. Green powder product was obtained as a final product. The yield was about 63%.

Synthesis Example 16

Synthesis of bis[bis[(5-bithiophene-2-yl]-1,4-phenylenediyl]amino-1,1'-biphenyl)]-N,N'-bis[4-(1,1-dimethylethyl)phenyl]-N,N'-bis(1,4-phenylenediyl)-(1,1'-biphenyl)-4,4'-diamine (TPD-TPA-4T2)

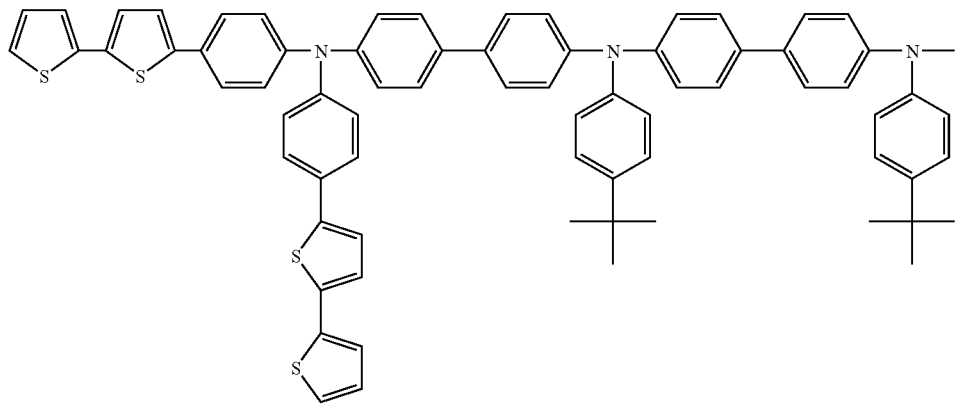

[compound 16]

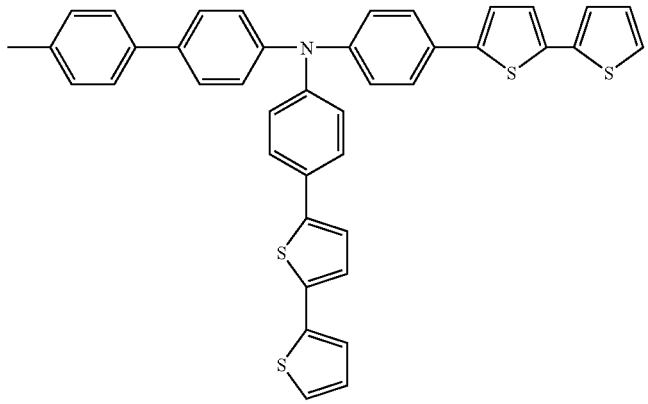

To a dry air-tight reactor equipped with a mechanical stirrer and connectable to a nitrogen line and a vacuum line were added N,N'-bis[4-(1,1-dimethylethyl)phenyl]-N,N'-bis(1,4-phenylenediyl)-(1,1'-biphenyl)-4,4'-diamine-4,4'-bis-4,4,5,5-tetramethyl-1,3,2-dioxaborolane (426 mg, 0.5 mmol), tris(4-bromophenyl)amine (482 mg, 1 mmol), Suzuki coupling catalyst, toluene 5 ml, tetraethylammonium hydroxide (20 wt %) 8 ml to cause reaction. The reactor was evacuated and purged with nitrogen 3 times and was heated to 95° C. The reaction was kept at 95° C. under nitrogen for about 4.5 hours. Next, 5-(4,4,5,5-tetramethyl-1,3,2-dioxaborolane-2-yl)-2,2'-bithiophene (614 mg, 2.1 mmol) was added and the reaction was kept at 95° C. under nitrogen for further 5 hours.

After cooling the reaction product, the reaction product was added dropwise to 200 ml of methanol to precipitate the product. Next, the product was washed with methanol 3 times. After drying under vacuum, the product was dissolved in 10 ml of chloroform and refined by column chromatography filled with silica gel. After removing the solvent by a rotary evaporator to condense to proper amount, the product was added dropwise to 200 ml methanol to precipitate the product. The precipitate was washed with methanol 3 times and dried under vacuum. Green powder product was obtained as a final product. The yield was about 82%.

Synthesis Example 17

Synthesis of poly[(9,9-dioctylfluorene-2,7-diyl)-co-(bithiophene-2,5'-diyl)-co-N,N'-bis[4-(1,1-dimethylethyl)phenyl]-N,N'-bis(1,4-phenylenediyl)-(1,1'-biphenyl)-4,4'-diamine-co-(4''-trithiophenephenylene-1,4-diyl)-di(1,4-phnylenediyl)amine] (PF8-T2(40%)-TPD(25%)-TPA (10%))

[compound 17]

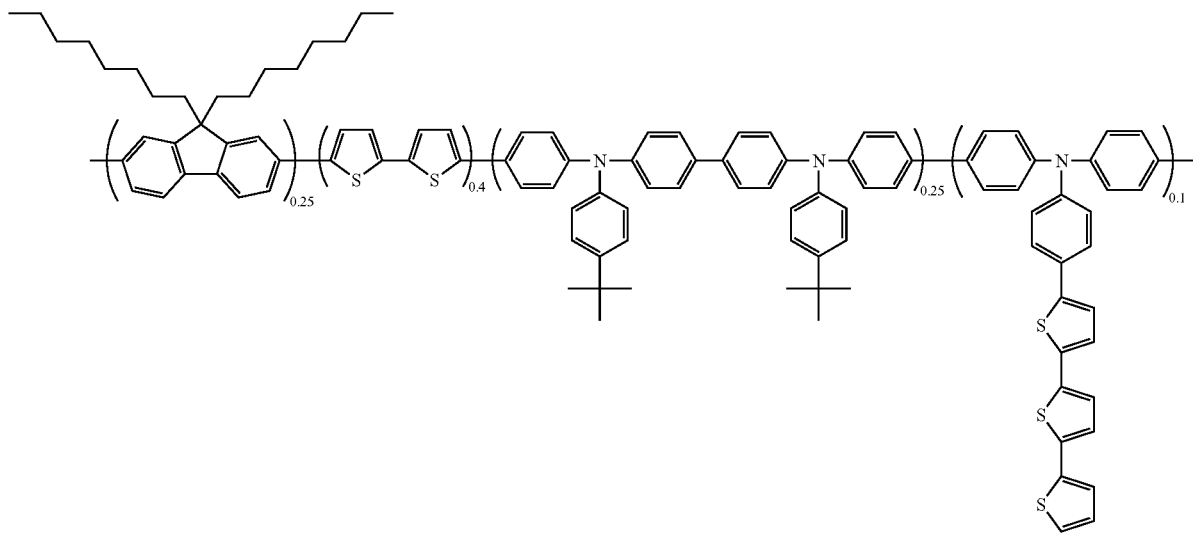

To a dry air-tight reactor equipped with a mechanical stirrer and connectable to a nitrogen line and a vacuum line were added N,N'-bis[4-(1,1-dimethylethyl)phenyl]-N,N'-bis(1,4-phenylenediyl)-(1,1'-biphenyl)-4,4'-diamine-4,4'-bis(4,4,5,5-tetramethyl-1,3,2-dioxabolorane (213 mg, 0.25 mmol), 9,9-dioctylfluorene-2,7-bis(4,4,5,5-tetramethyl-1,3,2-dioxabolorane (160.5 mg, 0.25 mmol), 2,5'-dibromobithiophene (130 mg, 0.4 mmol), tris(4-bromophenyl)amine (48.2 mg, 0.1 mmol), 5-(4,4,5,5-tetramethyl-1,3,2-dioxabolorane-2-yl)-2,2',2'-tarthiophene (37.5 mg, 0.2 mmol), Suzuki coupling catalyst, toluene 5 ml, tetraethylammonium hydroxide (20 wt %) 8 ml to cause reaction. The reactor was evacuated and purged with nitrogen 3 times and was heated to 95° C. The reaction was kept at 95° C. under nitrogen for about 3 hours. Next, phenylboronic acid 61 mg was added and the reaction was kept at 95° C. under nitrogen for further 2 hours. Thereafter, about 0.12 mg of bromobenzene was added and the reaction was kept at 95° C. under nitrogen for further 2 hours.

After cooling the reaction product, the reaction product was added dropwise to 300 ml of methanol to precipitate the product. Next, the product was washed with methanol 3 times. After drying under vacuum, the product was dissolved in 10 ml of toluene and refined by column chromatography filled with silica gel. After removing the solvent by a rotary evaporator to condense to proper amount, the product was added dropwise to 300 ml methanol to precipitate the product. The precipitate was washed with methanol 3 times and dried under vacuum. Yellow powder product was obtained as a final product. The yield was about 58%.

Synthesis Example 18

Synthesis of bis[bis[(5,2'-bithiophene-2-yl]-1,4-phenylenediyl]amino-1,4-phenylenediyl]-5,2'-bithiophene-2,5'-diyl (T2-TPA-4T2)

[compound 18]

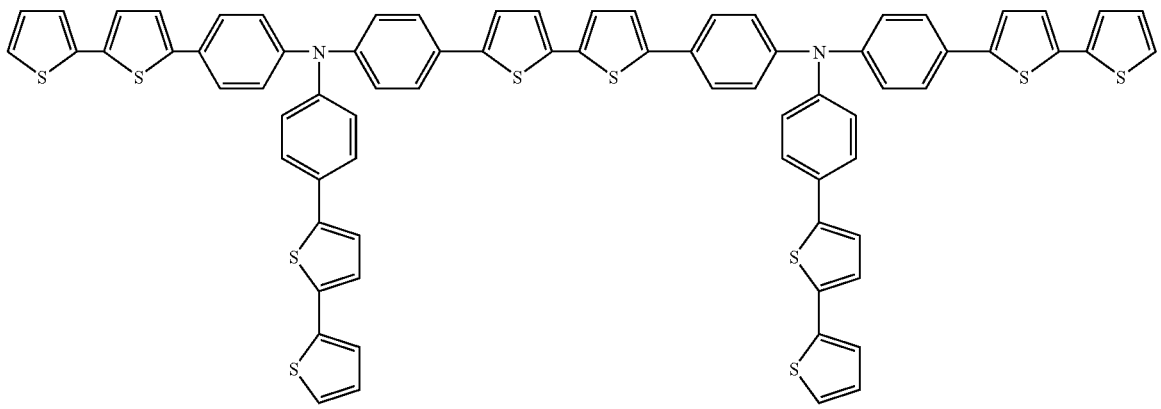

To a dry air-tight reactor equipped with a mechanical stirrer and connectable to a nitrogen line and a vacuum line were added 5,5'-di(4,4,5,5-tetramethyl-1,3,2-dioxaborolane-2-yl)-2,2'-bithiophene (209 mg, 0.5 mmol), tris(4-bromophenyl)amine (482 mg, 1 mmol), Suzuki coupling catalyst, toluene 5 ml, tetraethylammonium hydroxide (20 wt %) 8 ml to cause reaction. The reactor was evacuated and purged with nitrogen 3 times and was heated to 95° C. The reaction was kept at 95° C. under nitrogen for about 4.5 hours. Next, 5-(4,4,5,5-tetramethyl-1,3,2-dioxaborolane-2-yl)-2,2'-bithiophene (614 mg, 2.1 mmol) was added and the reaction was kept at 95° C. under nitrogen for further 5 hours.

After cooling the reaction product, the reaction product was added dropwise to 200 ml of methanol to precipitate the product. Next, the product was washed with methanol 3 times. After drying under vacuum, the product was dissolved in 10 ml of chloroform and refined by column chromatography filled with silica gel. After removing the solvent by a rotary evaporator to condense to proper amount, the product was added dropwise to 200 ml methanol to precipitate the product. The precipitate was washed with methanol 3 times and dried under vacuum. Yellow powder product was obtained as a final product. The yield was about 48%.

Synthesis Example 19

Synthesis of 2,7-di(5,2',5',2",5",2'''-tetrathiophene-2-yl)-9,9-dioctylfluorene (F8-4T)

To a dry air-tight reactor equipped with a mechanical stirrer and connectable to a nitrogen line and a vacuum line were added 9,9-dioctylfluorene-2,7-bis(4,4,5,5-tetramethyl-1,3,2-dioxaborolane (321 mg, 0.5 mmol), 2,5'-dibromobithiophene (324 mg, 1.0 mmol), Suzuki coupling catalyst, toluene 5 ml, tetraethylammonium hydroxide (20 wt %) 8 ml to cause reaction. The reactor was evacuated and purged with nitrogen 3 times and was heated to 95° C. The reaction was kept at 95° C. under nitrogen for about 4.5 hours. Next, 5-(4,4,5,5-tetramethyl-1,3,2-dioxaborolane-2-yl)-2,2'-bithiophene (307 mg, 1.05 mmol) was added and the reaction was kept at 95° C. under nitrogen for further 5 hours.

After cooling the reaction product, the reaction product was added dropwise to 200 ml of methanol to precipitate the product. Next, the product was washed with methanol 3 times. After drying under vacuum, the product was dissolved in 10 ml of chloroform and refined by column chromatography filled with silica gel. After removing the solvent by a rotary evaporator to condense to proper amount, the product was added dropwise to 200 ml methanol to precipitate the product. The precipitate was washed with methanol 3 times and dried under vacuum. Yellow powder product was obtained as a final product. The yield was about 45%.

Organic Transistor Fabrication: Examples 1 to 9 and Comparative Example 1

MOS type field effect transistors were fabricated using the organic semiconductor materials synthesized above in the same manner as Examples 1 to 9.

Example 10

An organic transistor was fabricated by forming the organic semiconductor film 3 using the compound 14 and the characteristics of the obtained organic transistor were evaluated as described above. The channel length L was 0.1 mm and the channel width W was 1 mm.

Figure 12:
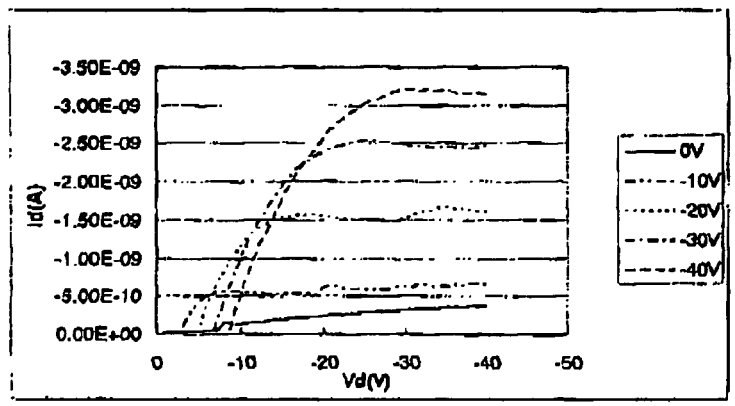
FIG. 12 is a drawing showing V-I characteristic of the organic transistor fabricated in Example 10.

FIG. 12 is a drawing showing the V-I characteristic. The on/off ratio was 8 and the mobility was $2.35 \times 10^{-5}$ cm$^2$/VS and thus good transistor characteristics were obtained.

Example 11

An organic transistor was fabricated by forming the organic semiconductor film 3 using the compound 15 and the characteristics of the obtained organic transistor were evaluated as described above. The channel length L was 0.07 mm and the channel width W was 1 mm.

[compound 19]

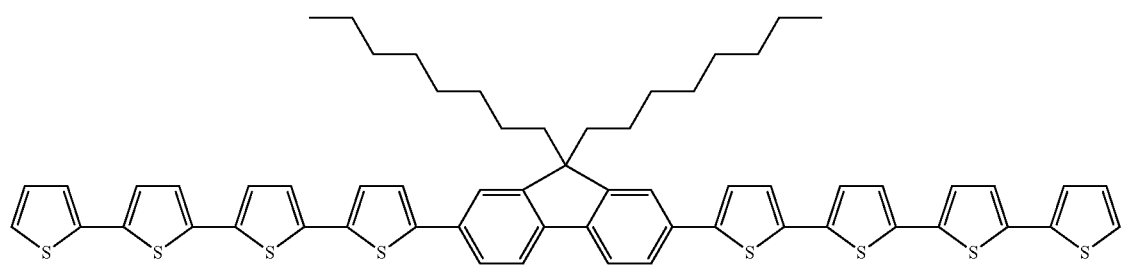

Figure 13:
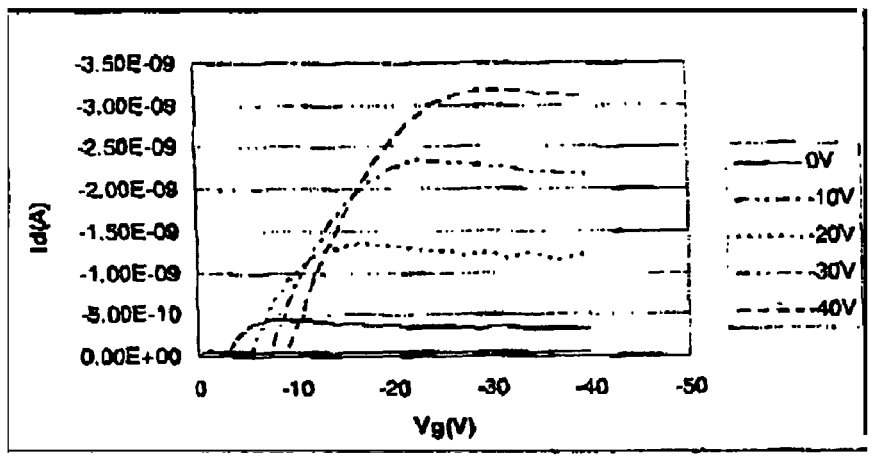
FIG. 13 is a drawing showing V-I characteristic of the organic transistor fabricated in Example 11.

FIG. 13 is a drawing showing the V-I characteristic. The on/off ratio was 71 and the mobility was $1.61 \times 10^{-5}$ cm$^2$/VS and thus good transistor characteristics were obtained.

Example 12

An organic transistor was fabricated by forming the organic semiconductor film 3 using the compound 16 and the characteristics of the obtained organic transistor were evaluated as described above. The channel length L was 0.1 mm and the channel width W was 1 mm.

Figure 14:
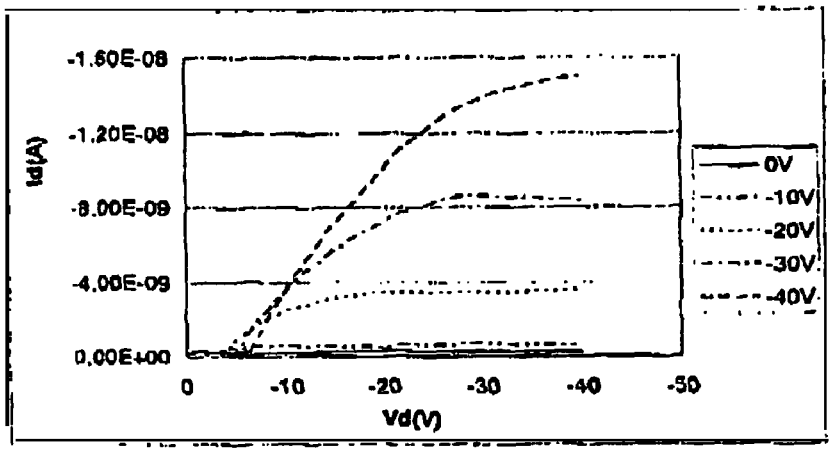
FIG. 14 is a drawing showing V-I characteristic of the organic transistor fabricated in Example 12.

FIG. 14 is a drawing showing the V-I characteristic. The on/off ratio was 56 and the mobility was $9.2 \times 10^{-5}$ cm$^2$/VS and thus good transistor characteristics were obtained.

Example 13

An organic transistor was fabricated by forming the organic semiconductor film 3 using the compound 17 and the characteristics of the obtained organic transistor were evaluated as described above. The channel length L was 0.1 mm and the channel width W was 1 mm.

Figure 15:
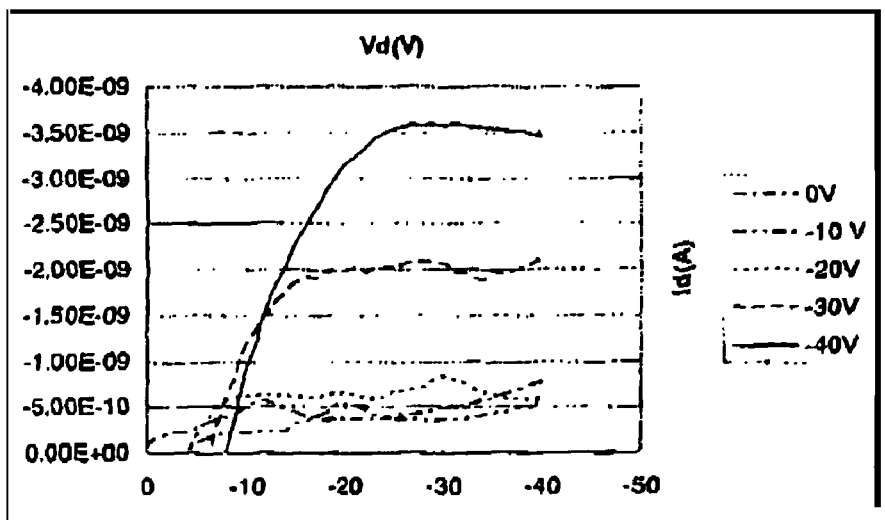
FIG. 15 is a drawing showing V-I characteristic of the organic transistor fabricated in Example 13.

FIG. 15 is a drawing showing the V-I characteristic. The on/off ratio was 5 and the mobility was $5.2 \times 10^{-5}$ cm$^2$/VS and thus good transistor characteristics were obtained.

Example 14

An organic transistor was fabricated by forming the organic semiconductor film 3 using the compound 18 and the characteristics of the obtained organic transistor were evaluated as described above. The channel length L was 0.05 mm and the channel width W was 1 mm.

The on/off ratio was 8 and the mobility was $4.6 \times 10^{-5}$ cm$^2$/VS and thus good transistor characteristics were obtained.

Comparative Example 2

An organic transistor was fabricated by forming the organic semiconductor film 3 using the compound 19. However, even if the gate voltage was changed, no modulation of the drain current was observed.

Accordingly, the organic transistors comprising the organic semiconductor films formed using the organic semiconductor materials of the invention had good transistor characteristics. Consequently, the organic semiconductor material according to the invention has a high carrier mobility and suitable for giving good transistor characteristics if being used for the organic transistor.

What is claimed is:

1. An organic semiconductor material comprising an amine unit having a secondary or tertiary amine structure and a thiophene unit having a thiophene ring structure, wherein said organic semiconductor material comprises one of the following structures:

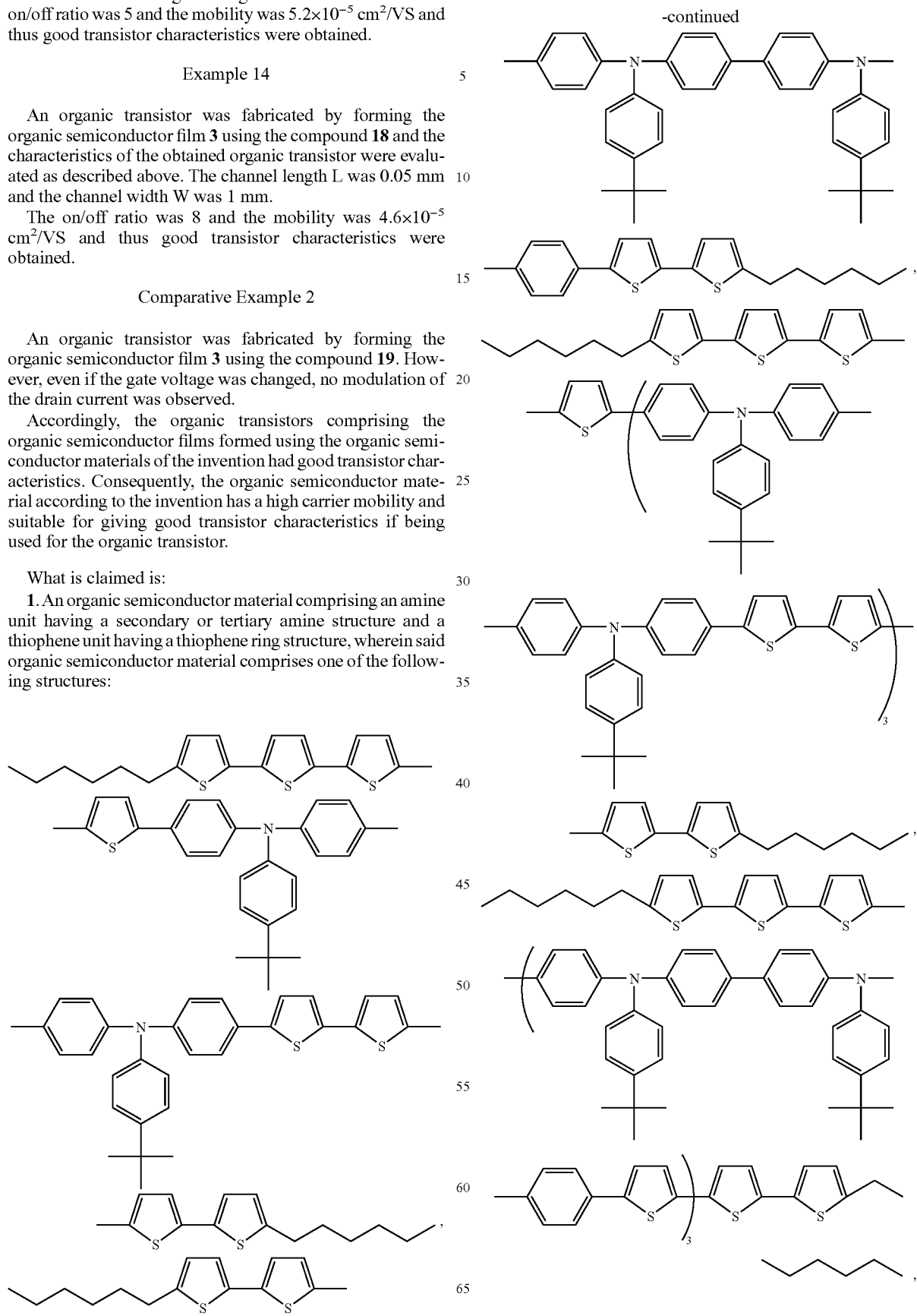

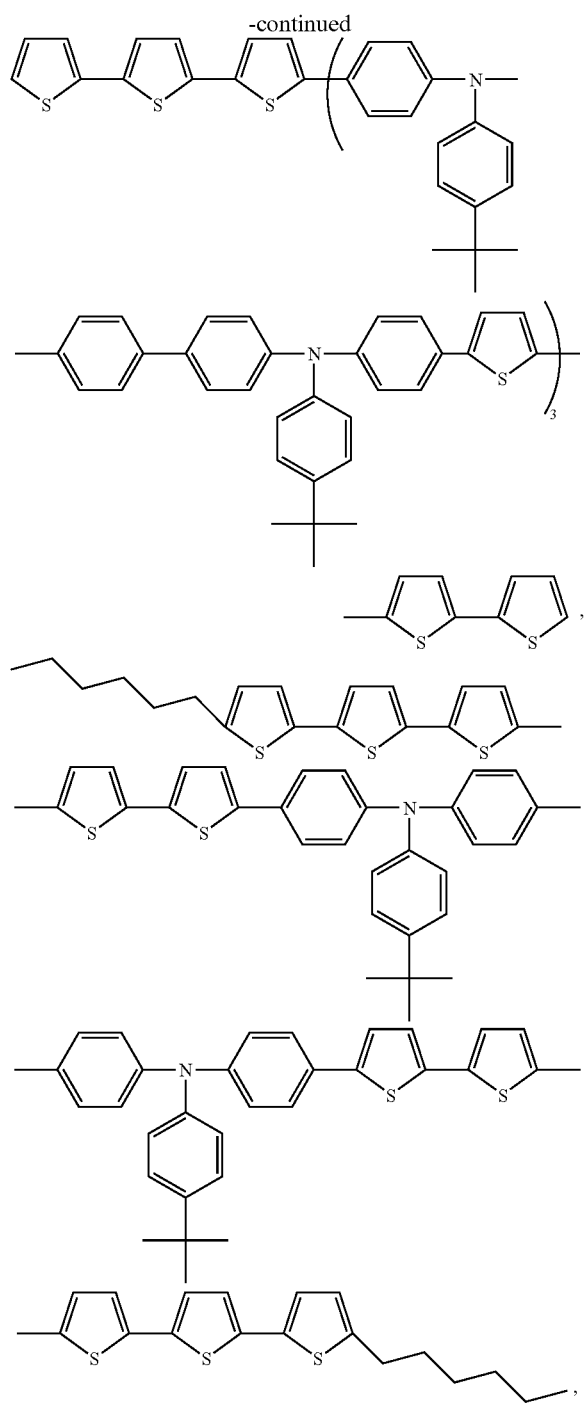

2. An organic semiconductor element comprising the organic semiconductor material according to claim 1.

3. An organic transistor comprising the organic semiconductor material according to claim 1.

4. A field effect transistor comprising a charge transporting material layer and a gate electrode directly or indirectly contacting the charge transporting material layer, wherein the charge transporting material layer is formed using the organic semiconductor material according to claim 1.

* * * * *